United States Patent [19]

Tuomanen et al.

[11] Patent Number: 5,665,561
[45] Date of Patent: Sep. 9, 1997

[54] MODULATORS OF PNEUMOCOCCAL ADHERENCE TO PULMONARY AND VASCULAR CELLS AND DIAGNOSTIC AND THERAPEUTIC APPLICATIONS

[75] Inventors: Elaine I. Tuomanen; Diana R. Cundell, both of New York, N.Y.

[73] Assignee: The Rockefeller University, New York, N.Y.

[21] Appl. No.: 254,577

[22] Filed: Jun. 6, 1994

[51] Int. Cl.$^6$ .............................. C12Q 1/04; C12Q 1/02; C12Q 1/14; A01N 43/04
[52] U.S. Cl. .................. 435/34; 435/29; 435/4; 435/7.34; 435/36; 435/14; 435/885; 435/975; 514/53; 514/62; 536/1.11; 536/4.1; 536/123.1
[58] Field of Search ...................... 435/34, 29, 4, 435/810, 7.34, 36, 14, 885, 975; 514/53, 54, 62; 536/1.11, 4.1, 123.1

[56] References Cited

U.S. PATENT DOCUMENTS

| | | | |
|---|---|---|---|
| 4,704,360 | 11/1987 | Shoham et al. | 435/7.34 |
| 5,089,479 | 2/1992 | Krivan et al. | 435/34 |
| 5,180,674 | 1/1993 | Roth | 435/288 |
| 5,217,715 | 6/1993 | Krivan et al. | 435/34 |
| 5,225,330 | 7/1993 | Ginsburg et al. | 435/34 |
| 5,288,637 | 2/1994 | Roth | 435/288 |
| 5,386,027 | 1/1995 | Krivan et al. | 536/1.11 |
| 5,389,521 | 2/1995 | Krivan et al. | 435/7.34 |
| 5,399,567 | 3/1995 | Platt et al. | 514/53 |

FOREIGN PATENT DOCUMENTS

| | | |
|---|---|---|
| 0126043 | 2/1984 | European Pat. Off. |
| WO91/16449 | 10/1991 | WIPO |
| WO93/13198 | 7/1993 | WIPO |
| 94/03184 | 2/1994 | WIPO |

OTHER PUBLICATIONS

Andersson et al, Jour. Infectious Diseases, vol. 153 (2), pp. 232–237, 1986.
Lee et al., 1994, Mol. Microbiol. 11:705–13.
Gbarah et al. 1993. Infect. Immun. 61: 1687–93.
Geelen et al., 1993, Infect. Immun. 61:1538–43.
Karlsson, 1989, Annu. Rev. Biochem. 58:309–50.
Krivan et al., 1988, Proc. Natl. Acad. Sci. USA 85:6157–61.
Tuomanen et al., 1988, J. Exp. Med. 168:267–77.
Plotkowski, 1986, Am. Rev. Respir. Dis. 134:1040–44.
Tuomanen et al., 1985, J. Infect. Dis. 151:859–68.
Andersson et al., 1983, J. Exp. Med. 158:559–70.
Andersson et al., 1981, Infect. Immun. 32:311–17.
Hakamori, 1981, Sem. Hematol. 18:39–62.

(List continued on next page.)

*Primary Examiner*—John Kight
*Assistant Examiner*—Louise Leary
*Attorney, Agent, or Firm*—Klauber & Jackson

[57] ABSTRACT

The present invention relates to compositions and methods for preventing pneumococcal infection. In particular, this invention relates to the identification of the minimum receptor targets of pneumococcal adherence to pulmonary and vascular endothelium, and to compositions and methods for preventing such adherence. In particular, the invention relates to the ability of one or more carbohydrate entities having the following motif or motifs: a disaccharide N-acetyl-D-galactosamine β1-3Gal motif, a disaccharide N-acetyl-D-galactosamine β1-4Gal motif, and an N-acetyl-D-glucosamine motif, effective to induce elution of adherent *S. pneumoniae* from host cells. In particular, a composition containing all three motifs can elute about 100% of pneumococcal bacteria from lung epithelial cells, and from venous endothelial cells. In a particular embodiment, a pharmaceutical composition of the invention can be used to treat pneumococcal infections in which the host cells are lung epithelial cells. For use in blocking adherence to, or eluting adherent bacteria from, lung epithelial cells, the pharmaceutical composition is an aerosol formulation. The invention further provides formulations for parenteral administration for treating systemic blood-borne infections by preventing or reversing binding to venous endothelial cells. The invention further relates to methods and kits for determining the presence of pneumococci in a biological sample from a subject.

42 Claims, 9 Drawing Sheets

OTHER PUBLICATIONS

Dobbs and Mason, 1979, J. Clin. Invest. 63:378–87.
Cundell et al. (1995) Infect. Immun. (Mar.):757–61.
Cundell et al. (1994) Microb. Pathog. 17:361–74.
Sundberg–kovamees et al. (1994) Microbial Patthogenesis 17:63–8.
Beuth et al. (1987) Zentralbl Bakteriol Mikrobiol Hyg. 265:160–8.
Andersson et al. (1984) Otolaryngology–Head and Neck Surgery 92:266–9.

MODULATORS OF PNEUMOCOCCAL ADHERENCE TO PULMONARY AND VASCULAR CELLS AND DIAGNOSTIC AND THERAPEUTIC APPLICATIONS

The research leading to this invention was supported in part by Grant No. RO1-A1-27913 from the National Institution of Allergy and Infectious Disease. The Government may have certain rights in the invention.

FIELD OF THE INVENTION

The present invention relates to compositions and methods for preventing pneumococcal infection. In particular, this invention relates to the identification of the targets of pneumococcal adherence to pulmonary and vascular endothelium, and to compositions and methods for preventing such adherence.

BACKGROUND OF THE INVENTION

*Streptococcus pneumoniae* is the most frequent cause of bacterial pneumonia in children of developing countries and accounts for up to 76% of cases in adults (Pennington, 1986, Am. Fam. Physician 33:153; Johnston, 1991, Revs. Infect. Dis. 13 (Suppl. 6):S509; Musher, 1992, Clin. Infect. Dis. 14:801). Pneumococci generally enter the host via the nasopharynx where they attach to epithelial cells and in some instances persist for several months (Anderson et al., 1981, Infect. Immun. 32:311). In experimental models, progression to pneumonia results from spread of the pneumococci by aerosolization and conveyance from the nasopharynx down into the lower respiratory tract.

The early pneumonic lesion is characterized by fluid filled alveoli containing pneumococci, which are frequently seen to line the alveolar walls, a distribution suggestive of a specific interaction promoting retention in the alveolar space (Wood, 1941, J. Exp. Med. 73:222). Pneumococci readily gain access to the blood circulation from the alveolar space, suggesting an aggressive capability to cross the vascular endothelial cells of the alveolar capillaries (Rake, 1936, J. Exp. Med. 63:191).

Bacterial adherence to eukaryotic cells commonly involves specific bacterial proteins (adhesions) which recognize host cell glycoconjugates. Adherence of pneumococci to human oral epithelium is inhibited in the presence of the disaccharide N-acetyl-glucosamine-β1-3-galactose (GlcNAcβ1-3Gal) suggesting that this carbohydrate can serve as a receptor, perhaps relevant to nasopharyngeal carriage (Anderson et al., 1983, J. Exp. Med. 158:559). It remains unknown precisely which cell type supports pneumococcal adherence in the alveolar space. Pneumococci have been reported to bind to purified glycoconjugates containing terminal or internal GalNAcβ1-4Gal, a structure prevalent in pulmonary secretions and lung tissue (Krivan et al., 1988, Proc. Natl. Acad. Sci. USA 85:6157). This structure differs significantly in stereochemistry from that proposed for the nasopharyngeal receptor.

The identity of pneumococcal adhesions capable of mediating attachment to the nasopharynx and lung is unknown. Consistent with the ability to readily cause experimental bacteremia, pneumococcal adherence to vascular endothelial cells has been shown to be dose-dependent, rapid and independent of capsular type (Geelen et al., 1993, Infec. Immun. 61:1538). Both cell-wall components and protein components contribute roughly equally to this association, but specific pneumococcal ligands remain to be identified (Tuomanen et al., 1985, J. Infect. Dis. 151:859).

The citation of references herein shall not be construed as an admission that such is prior art to the present invention.

SUMMARY OF THE INVENTION

In a first aspect, the present invention is directed to a pharmaceutical composition comprising an amount of a carbohydrate containing a disaccharide N-acetyl-D-galactosamine β1-3Gal motif effective to induce elution of adherent *Streptococcus pneumoniae* from host cells. The disaccharide may be linked to mannose. The carbohydrate component of the pharmaceutical composition of the invention can competitively inhibit the binding of pneumococci to host cells, particularly lung epithelial cells and vascular endothelial cells. Competitive inhibition of pneumococcal binding, termed herein "adhesion," can prevent colonization of susceptible host cells by pneumococci, or elute adherent pneumococci from host cells.

Thus, a particular advantage of the invention is that it provides a treatment for pneumococci that is independent of antibiotics. More particularly, the present invention can be efficacious for treating antibiotic and multiple antibiotic resistant bacteria. Alternatively, the pharmaceutical compositions and methods of the present invention can be used in conjunction with antibiotics to treat an infection suspected of or known to be a pneumococcal infection.

In a more preferred embodiment, the pharmaceutical composition comprises an amount of a second carbohydrate containing a disaccharide N-acetyl-D-galactosamine β1-4Gal motif effective to induce elution of adherent *S. pneumoniae* from host cells. This second group can also be linked to mannose.

A further discovery of the invention is that activated host cells exhibit yet another saccharide specificity for pneumococcal adhesion: N-acetyl-D-glucosamine (GlcNAc). Accordingly, in another preferred embodiment, the pharmaceutical composition comprises an amount of a third carbohydrate containing an N-acetyl-D-glucosamine motif effective to induce elution of adherent *S. pneumoniae* from host cells.

In the most preferred embodiment, the pharmaceutical composition of the invention comprises an amount of each of the three carbohydrates, a carbohydrate containing a disaccharide N-acetyl-D-galactosamine β1-3Gal motif, a second carbohydrate containing a disaccharide N-acetyl-D-galactosamine β1-4Gal motif, and a third carbohydrate containing an N-acetyl-D-glucosamine motif, effective to induce elution of adherent *S. pneumoniae* from host cells. In particular, this composition can elute about 100% of pneumococcal bacteria from lung epithelial cells, and from venous endothelial cells.

The inventors herein have observed that additional carbohydrate groups can be included in a composition of the invention. For example, but not by way of limitation, a composition of the invention may further comprise an amount of one or more of mannose, N-acetyl-D-galactosamine, mannose-D-mannose, and methyl-α-D-mannopyranoside effective to inhibit binding of pneumococci to a host cell.

In a preferred aspect, the carbohydrates contain a multiplicity of pneumococcal binding motifs, i.e., the carbohydrates are polyvalent or multivalent. In one embodiment, a carbohydrate is multivalent for one motif. In another embodiment, a carbohydrate contains more than one motif, and may be multivalent for each. Multivalence can be achieved using branching complex oligosaccharides; alternatively, monovalent carbohydrates can be conjugated to a polymer carrier, such as a protein, cyclodextran, polylysine, polyacrylamide, agarose, SEPHAROSE, and the like. Preferably, 20 to 30 such motifs are attached to each polymer.

In a particular embodiment, a pharmaceutical composition of the invention can be used to treat pneumococcal infections in which the host cells are lung epithelial cells. For use in blocking adherence to, or eluting adherent bacteria from, lung epithelial cells, the pharmaceutical composition is an aerosol formulation, which formulation contains a dispersant. For example, the dispersant can be a surfactant. In one specific embodiment, the aerosol formulation is a dry powder aerosol formulation, in which the carbohydrate or carbohydrates are present in finely divided powder. In another embodiment, the aerosol formulation is a liquid aerosol formulation, which includes a pharmaceutically acceptable diluent. Possible diluents include, but are not limited to, sterile water, saline, buffered saline, and dextrose solution.

The present invention further extends to a pharmaceutical composition that can be used to treat pneumococcal infections that have spread into the blood, in which the host cells are vascular endothelial cells. Pneumococcal infection of blood follows pulmonary infection with significant frequency, and can lead to severe complications, such as but not limited to, sepsis, bacteremia, and meningitis. Thus, the invention relates to pharmaceutical compositions for injection into the blood, in particular for intravenous injection, to treat pneumococcal infections that have spread into the blood.

Accordingly, the invention relates to a method for preventing or treating an infection with S. pneumoniae comprising administering to a subject believed to be in need of such treatment an amount of a carbohydrate containing mannose linked to a disaccharide N-acetyl-D-galactosamine β1-3Gal group effective to induce elution of adherent S. pneumoniae from host cells. In a preferred embodiment, the method further comprises administering an amount of a second carbohydrate containing mannose linked to a disaccharide N-acetyl-D-galactosamine β1-4Gal group effective to induce elution of adherent S. pneumoniae from host cells. In another preferred embodiment, the method further comprises administering an amount of a third carbohydrate containing N-acetyl-D-glucosamine effective to induce elution of adherent S. pneumoniae from host cells. In the most preferred embodiment, the method comprises administering an amount of each of the three carbohydrates, a carbohydrate containing mannose linked to a disaccharide N-acetyl-D-galactosamine β1-3Gal group, a second carbohydrate containing mannose linked to a disaccharide N-acetyl-D-galactosamine β1-4Gal group, and a third carbohydrate containing N-acetyl-D-glucosamine, effective to induce elution of adherent S. pneumoniae from host cells.

As noted above, the invention particularly relates to treating infections of lung epithelial cells. Accordingly, a method for treating an infection with S. pneumoniae comprises atomizing and inhaling the carbohydrate or carbohydrates. Preferably, the atomization is with a nebulizer to create a sonicated mist that is readily inhaled.

The invention also particularly relates to treating infections of the blood. Accordingly, a method for treating a blood infection with *S. pneumoniae* comprises injecting the carbohydrate or carbohydrates intravenously.

In another aspect, the present invention relates to a method for detecting the presence of *S. pneumoniae* comprising detecting the binding of a carbohydrate containing mannose linked to a disaccharide N-acetyl-D-galactosamine β1-3Gal group to bacteria. In a further embodiment, detecting the presence of pneumococci further comprises detecting the binding of a second carbohydrate containing mannose linked to a disaccharide N-acetyl-D-galactosamine β1-4Gal group to bacteria. In another embodiment, the detecting the presence of pneumococci further comprises detecting the binding of a third carbohydrate containing N-acetyl-D-glucosamine to bacteria.

In the most preferred embodiment, the method for detecting the presence of S. pneumoniae comprises detecting the binding of all three carbohydrate to bacteria.

According to the invention, the carbohydrate or carbohydrates are detectably labeled; alternatively, the carbohydrate or carbohydrates may be attached to a solid phase support.

BRIEF DESCRIPTION OF THE DRAWINGS

FIG. 1. Adherence of pneumococci to primary rabbit pneumocytes. A) Adherence of encapsulated AII to mixed lung cells (○—○) and purified Type II lung cells (■—■). B) Comparison of the binding of encapsulated AII (■—■) and isogenic, unencapsulated R6 pneumococci (○—○) to Type II lung cells. For both panels, adherent bacteria were enumerated by plating for cfu and by visualization by Gram stain. Values are the means ±SD of six experiments. *$p<0.05$ versus mixed lung cells.

FIG. 2. Dose-response curve (A) and time course (B) for adherence of pneumococci to human cultured Type II pneumocytes. For the dose-responsive curve, Type II pneumocytes were incubated with increasing concentration of AII (■—■), R6 (□—□), D39 (○—○), 18C (▲—▲) or 9V (Δ—Δ) for 30 min. For the time, course experiments type II pneumocytes were incubated with $1\times10^7$ cfu/ml R6. Adherent bacteria were determined as the number of attached bacteria per 100 type II lung cells. Results are the means ±SD for duplicate wells in at least six independent experiments.

FIG. 3. Effect of glycolipids containing the sequences GalNAcβ1-4Gal and GalNAcβ-3Gal on pneumococcal adherence to human cultured lung cells (A) and endothelial cells (B). R6 was incubated with GalNAcβ1-4Gal-containing glycolipids [asialo-GM2 (●—●) or asialo-GHM1 (○—○)] or GalNAcβ1-3Gal-containing glycolipids [forssman glycolipid (□—□) or globoside (■—■)]. Adherent bacteria were determined as the number of attached bacteria per 100 lung cells or endothelial cells. Control adherence in the absence of sugar is indicated by the horizontal line (---). Results are the means ±SD of duplicate well sin at least six independent experiments.

FIG. 4. Antiadherence effect of globoside, asialo-GM2 and purified pneumococcal cell wall. A) R6 was incubated with either albumin buffer (---), globoside (■—■) or asialo-GM2 (●—●) or the combination of asialo-GM2 plus globoside (♦—♦); final concentration indicated was composed equally of the 2 sugars) and allowed to adhere to Type II lung cell monolayers. *$p<0.05$ compared to asialo-GM2 or globoside alone.

B) Monolayers were incubated (30 min., 37° C.) with either pneumococcal cell wall (50 μg/ml) or albumin buffer. R6 was incubated (15 min., room temperature) with wither albumin buffer (control), globoside (2 mM) or asialo-GM2 (2 mM) and allowed to adhere to the monolayers for 30 min. at 37° C. Adherent bacteria were determined as the number of attached bacteria per 100 endothelial cells. Results are the means ±SD of duplicate wells in at least six independent experiments. Wall is significantly less than control * is significantly less than wall ($p<0.05$).

FIG. 5. Minimal carbohydrate receptor structures involved in pneumococcal adherence to two separate classes of receptor (A, B) on cultured human Type II pneumocytes and endothelial cells. Bold typed, boxed areas represent active minimal receptor unit required for adherence of pneumococci to Type II pneumocytes or endothelial cells. Structures underlined are inactive in both cell types. Abbreviations as per Table 1, infra.

FIG. 6. Effect of simple sugars on adherence of R6 resting and cytokine-stimulated human cultured type II pneumocytes (A) and vascular endothelial cells (B). R6 ($10^7$ cfu/ml) was exposed to various simple sugars (15 min., room temperature) and then co-incubated with either resting (open bars) or cytokine-stimulated (solid bars) monolayers of cells for 30 min. Pneumococcal adherence to a designated sugar was defined as bacterial adherence to 100 host cells in the absence of sugar minus bacterial adherence to 100 host cells in the presence of sugar. Results are the means ±SD for duplicate wells in at least six independent experiments. Glc=D-glucose; Gal=D-galactose; Fuc=L-fucose; GalNAc - N-acetyl-D-galactosamine; GlcNAc - N-acetyl-D-glucosamine; Man=D-mannose; NANA=sialic acid; Lac= lactose; and 2-ADGG=2-acetamide-2-deoxy-3-O-B-D-galactopyranosyl-D-galactopyranose.

FIG. 7. Pneumococcal glycoconjugate receptors on cytokine-stimulated monolayers. The number of pneumococci adherent to the GalNAcβ1-4Gal population was define by asialo-GM2 (□—□) and those adherent to the GalNAcβ1-3Gal population by globoside (◊—◊). To define whether the carbohydrate specificities were contained in one or more receptors, the ability of two component mixtures of GlcNAc (o—o) plus either globoside (♦—♦) or asialo-GM2 (■—■) to impair pneumococcal adherence to a greater degree than each sugar alone was assessed. The test compositions contained the single sugar or equal amounts of the two sugars tested. Control adherence to TNFα-stimulated monolayers is indicated by the hatched line (---). * $p<0.05$ compared to asialo-GM2 or GlcNAc alone. Pneumococcal adherence to each designated sugar was determined from the bacterial adherence to 100 host cells in the absence of sugar minus bacterial adherence to 100 host cells in the presence of sugar. Results shown are the means ±SD for duplicate wells from at least six independent experiments.

DETAILED DESCRIPTION OF THE INVENTION

Figure 1A:
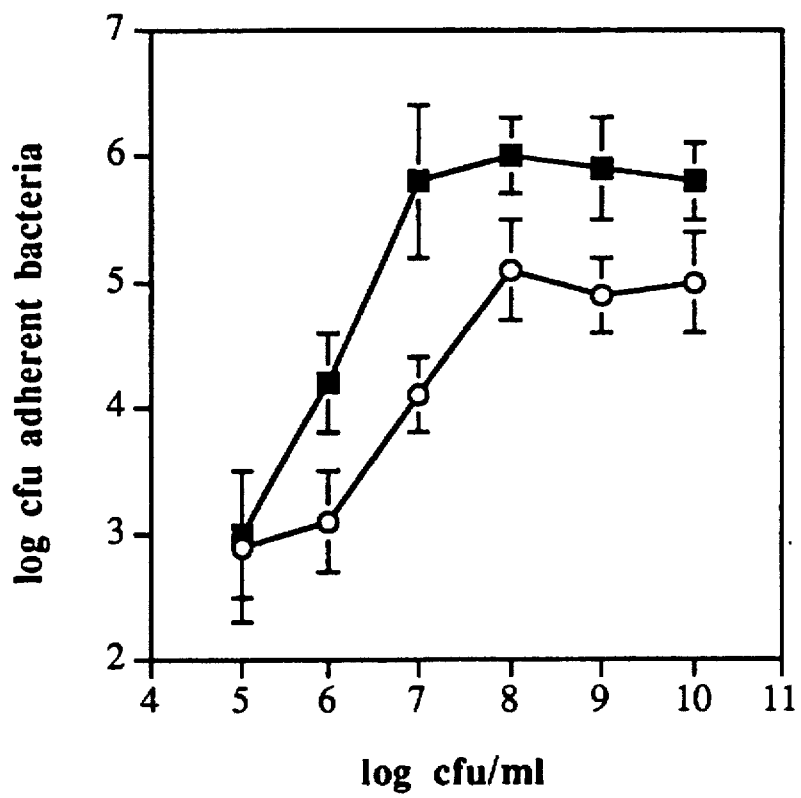

The present invention relates to compositions and methods for treating or preventing infection with S. pneumoniae. The present invention is based on the discovery that pneumococci recognize and bind to at least three different carbohydrate motifs, two of which were not recognized prior to this invention. In specific embodiments, the invention provides for inhibiting adhesion of pneumococci, or eluting adherent pneumococci, from lung epithelial cells.

The present inventors have discovered that a carbohydrate motif containing a GalNAcβ1-3Gal group binds to pneumococci. This motif was previously not known to interact with pneumococcus. More importantly, the inventors have discovered that pneumococci have more than one carbohydrate specificity, and that inhibiting binding to carbohydrates of only one such specificity cannot quantitatively elute the bacteria. Thus, using the preferred compositions and methods of the invention, quantitative elution (or prevention of adherence) can be achieved.

To provide a better understanding of the invention, definitions for certain terms are provided below; aspects of the invention—carbohydrates; therapeutic compositions and methods; diagnostic compositions and methods; and Examples are also presented.

A composition comprising "A" (where "A" is a single protein, DNA molecule, vector, etc.) is substantially free of "B" (where "B" comprises one or more contaminating proteins, DNA molecules, vectors, etc.) when at least about 75% by weight of the proteins, DNA, vectors (depending on the category of species to which A and B belong) in the composition is "A". Preferably, "A" comprises at least about 90% by weight of the A+B species in the composition, most preferably at least about 99% by weight. It is also preferred that a composition, which is substantially free of contamination, contain only a single molecular weight species having the activity or characteristic of the species of interest.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions.

As used herein, the term "host cell" refers to a cell capable of colonization by pneumococci, for example lung epithelial cells and venous endothelial cells.

As used herein, the term "pulmonary administration" refers to administration of a formulation of the invention into the lungs by inhalation.

As used herein, the term "inhalation" refers to intake of air to the alveoli. In specific examples, intake can occur by self-administration of a formulation of the invention while inhaling, or by administration via a respirator, e.g., to an patient on a respirator. The term "inhalation" used with respect to a formulation of the invention is synonymous with "pulmonary administration."

As used herein, the term "parenteral" refers to introduction of a carbohydrate that binds to pneumococcus into the body by other than the intestines, and in particular, intravenous (i.v.), intraarterial (i.a.), intraperitoneal (i.p.), intramuscular (i.m.), intraventricular, and subcutaneous (s.c.) routes. Preferably, the route is intravenous.

As used herein, the term "aerosol" refers to suspension in the air. In particular, aerosol refers to the particalization of a formulation of the invention and its suspension in the air. According to the present invention, an aerosol formulation is a formulation comprising a carbohydrate that is aerosolized, i.e., atomized and suspended in the air, for inhalation or pulmonary administration.

As used herein, the term "systemic" refers to a disease or disorder, or original site of injury distant to the lung or involving the entire body of the organism. The term "local" therefore is used herein with respect to the lung. Thus, a systemic infection is one in which S. pneumonia are found in the blood, and can lead to bacteremia and meningitis. A local infection is one in which the pneumococci have migrated only as far as the lung, and can lead to pneumonia.

The compositions of the invention, or the administration of a composition, can be used to protect or treat an animal subject from infection of *S. pneumoniae*. Thus, a composition of the invention can be used in birds, such as chickens, turkeys, and pets; in mammals, preferably a human, although the compositions of the invention are contemplated for use in other mammalian species, including but not limited to domesticated animals (canine and feline); farm animals (bovine, ovine, equine, caprine, porcine, and the like); rodents; and undomesticated animals.

Carbohydrate Motifs That Bind to Pneumococci

In its primary aspect, the present invention relates to the identification of the carbohydrate motifs that mediate adherence of pneumococci to host cells, in particular lung epithelial cells (Type II lung cells), and venous endothelial cells.

Thus, as used herein, the term "pneumococcal binding motif" refers to the structure of a carbohydrate that is recognized by the pneumococcal bacterial adhesion complex. It is well known that a carbohydrate (also termed oligosaccharide and saccharide) on a glycoprotein can be a highly complex structure formed by a set of monosaccharide (sugar) subunits arranged in a variety of linkages (see, e.g., Darnell et al., *Molecular Cell Biology*, Scientific American Books, 1986, pp. 957-964). The motif of the present invention is the minimum receptor unit, i.e., the minimum structure capable of binding with pneumococci, regardless of the "decoration" (additional saccharide subunits) found on the compound. Thus, the carbohydrate motif to which pneumococci bind can be located in a complex oligosaccharide, or may be the simplest possible oligosaccharide having the motif structure. Furthermore, a motif can be a derivative of the specific saccharide groups shown herein to mediate pneumococcal binding. A functional definition of a motif of the invention is that it can demonstrate pneumococcal binding and elution properties as described in the Examples herein.

As used herein, the term "carbohydrate" refers both to compounds containing saccharide subunits, and to such compounds associated or conjugated with a polymer as described herein.

In a first aspect, the invention relates to identification of a carbohydrate motif to which pneumococci bind that has not previously been known to mediate pneumococci binding. This motif contains a disaccharide N-acetyl-D-galactosamine β1-3Gal group (GalNAcβ1-3Gal). This motif may be, but need not be, linked to a mannose. Examples of carbohydrates that contain this motif include, but are not limited to, forssman glycolipid, globoside, etc.

In a further aspect, the inventors have discovered that quantitative or nearly quantitative elution of adherent pneumococci from host cells can be achieved by contacting the bacteria with the GalNAcβ1-3Gal motif and a second motif, to which pneumococci were previously known to adhere. This second motif is a carbohydrate containing a disaccharide N-acetyl-D-galactosamine β1-4Gal group (GalNAcβ1-4Gal). This motif may be, but need not be, linked to a mannose. Examples of carbohydrates that contain this second motif include, but are not limited to, asialo-GM1, asialo-GM2, etc. As shown in a specific example, infra, quantitative elution of pneumococci from unstimulated lung epithelial cells (Type II lung cells) and venous endothelial cells can be achieved by contacting these cells with a composition containing carbohydrates having both motifs.

In a further embodiment, the inventors herein have discovered that stimulation of the host cells to which pneumococci bind with inflammatory cytokines, such as tumor necrosis factor (TNF), interleukin-1 (IL-1), etc., induces a third previously unknown carbohydrate specificity: N-acetyl-D-glucosamine (GlcNAc). This sugar specificity is associated with the GalNacβ1-3Gal receptor population. Thus, a composition comprising a carbohydrate with the GalNAcβ1-3Gal motif and the GlcNAc motif (both motifs can be found on the same oligosaccharide, or on two different oligosaccharide) can be used to prevent adherence of pneumococci to, or elute adherent pneumococci from, host cells.

In the most preferred embodiment, a composition comprising carbohydrates that represent all three motifs can be used. Such a composition is particularly desirable to treat an early stage, ongoing infection, in which the immune system has been activated and inflammatory mediators have been released.

The invention contemplates including additional carbohydrate moieties that have been found to interfere with binding or adherence of pneumococci with host cells. Examples of such carbohydrates include, but are not limited to, mannose, N-acetyl-D-galactosamine, mannose-D-mannose, and methyl-α-D-mannopyranoside.

The present invention further contemplates use of multivalent carbohydrates or carbohydrate-containing structures to increase the potency of the drug. In one embodiment, one motif is found in multiple copies on a compound for use in the invention. In another embodiment, more than one motif is found in single or multiple copies on a compound for use in the invention. Multivalent carbohydrates can be prepared by preparing a branching complex carbohydrate, which conceptually resembles a tree or brush in which each branch or bristle contains a pneumococcal binding motif. Alternatively, monovalent carbohydrates can be associated covalently or non-covalently with a polymer (e.g., Langer et al., International Patent Publication No. WO 94/03184, published Feb. 17, 1994, which is specifically incorporated herein by reference). Suitable polymers include, but are not limited to, a protein, polylysine, dextran, a glycosaminoglycan, cyclodextrin, agarose, SEPHAROSE, and polyacrylamide.

Carbohydrates with pneumococcal binding motifs according to the invention can be obtained from any source. For example, such carbohydrates can be obtained from commercial sources. Alternatively, the carbohydrates can be prepared synthetically, using known chemical or enzymatic processes. Glycosyltransferase enzymes for synthesis of a carbohydrate (i.e., saccharide) that contains a pneumococcal binding motif can be prepared as described in International Patent Publication No. WO 93/13198 by Roth (published Jul. 8, 1993), which is incorporated herein by reference. Glycosyltransferase-catalyzed preparation of saccharide compositions has also been described (Roth, U.S. Pat. No. 5,180,674, issued Jan. 19, 1993, and International Patent Publication No. 91/16449, published Oct. 31, 1991), as has an apparatus for preparing such compositions (Roth, U.S. Pat. No. 5,288,637, issued Feb. 22, 1994) (each of these references is specifically incorporated herein by reference in its entirety).

Therapeutic Compositions and Methods

The present invention contemplates formulations comprising a carbohydrate containing a pneumococcal binding motif as described above for pulmonary or parenteral, especially i.v., administration for the prevention and treatment of pneumococcal infection, and resulting disease conditions including, but not limited to, bacteremia, meningitis, and pneumonia. Hereinafter, for convenience sake, the term "carbohydrate" in the singular or plural form should be interpreted to mean a carbohydrate containing a pneumococcal binding motif, unless another meaning is specifically provided.

Accordingly, the present invention provides pharmaceutical compositions comprising one or more carbohydrates containing a pneumococcal binding motif and a pharmaceutically acceptable carrier or excipient, as defined above. For the treatment of a nascent pneumococcal infection or a systemic infection, a therapeutic composition of the invention can be administered by inhalation, to prevent colonization of lung epithelial cells leading to infection, or to elute adherent bacteria from lung epithelial cells. Pulmonary administration is an effective mode of administration for the bloodstream as well, since drugs pass from the alveoli into the capillaries readily. Moreover since systemic pneumococcal infections generally begin with colonization of lung epithelial cells, administration of a therapeutic agent via the lungs is a rational route to treat the infection. Similarly, it is also possible for a drug administer parenterally, e.g., i.v., to cross from the capillaries to the alveoli. Accordingly, the present invention contemplates parenteral administration of a carbohydrate or carbohydrates, in particular i.v. administration, for treatment of both systemic and lung (local) pneumococcal infections.

Accordingly, a wide variety of devices that are designed for the delivery of pharmaceutical compositions and therapeutic formulations to the respiratory tract or parenterally can be used in this aspect of the invention. The preferred route of pulmonary administration of the present invention is in the aerosol or inhaled form. The carbohydrate or carbohydrates of the present invention, combined with a dispersing agent, or dispersant, can be administered in an aerosol formulation as a dry powder or in a solution or suspension with a diluent. However, as mentioned above, the composition of the invention can also be administered parenterally.

As used herein, the term "dispersant" refers to a agent that assists aerosolization of the carbohydrate or absorption of the carbohydrate in lung tissue, or both. Preferably the dispersant is pharmaceutically acceptable. For example, surfactant that are generally used in the art to reduce surface induced aggregation of the carbohydrates caused by atomization of the solution forming the liquid aerosol may be used. Non-limiting examples of such surfactant are surfactant such as polyoxyethylene fatty acid esters and alcohols, and polyoxyethylene sorbitan fatty acid esters. Amounts of surfactant used will vary, being generally within the range or 0.001 and 4% by weight of the formulation. Suitable surfactant are well known in the art, and can be selected on the basis of desired properties, depending on the specific formulation, concentration of carbohydrate or carbohydrates, diluent (in a liquid formulation) or form of powder (in a dry powder formulation), etc.

Moreover, depending on the choice of the carbohydrate or carbohydrates (e.g., disaccharide or complex oligosaccharide), the desired therapeutic effect, the quality of the lung tissue (e.g., diseased or healthy lungs), and numerous other factors, the liquid or dry formulations can comprise additional components, as discussed further below.

The liquid aerosol formulations contain the carbohydrate or carbohydrates and a dispersing agent in a physiologically acceptable diluent. The dry powder aerosol formulations of the present invention consist of a finely divided solid form of the carbohydrate or carbohydrates and a dispersing agent. The parenteral formulations contain the carbohydrate or carbohydrates in a suitable carrier for injection.

With either the liquid or dry powder aerosol formulation, the formulation must be aerosolized. That is, it must be broken down into liquid or solid particles in order to ensure that the aerosolized dose actually reaches the alveoli. In general the mass median dynamic diameter will be 5 micrometers or less in order to ensure that the drug particles reach the lung alveoli (Wearley, L. L., 1991, 1991, Crit. Rev. in Ther. Drug Carrier Systems 8:333). The term "aerosol particle" is used herein to describe the liquid or solid particle suitable for pulmonary administration, i.e., that will reach the alveoli. Other considerations such as construction of the delivery device, additional components in the formulation and particle characteristics are important. These aspects of pulmonary administration of a drug are well known in the art, and manipulation of formulations, aerosolization means and construction of a delivery device require at most routine experimentation by one of ordinary skill in the art.

With regard to construction of the delivery device, any form of aerosolization known in the art, including but not limited to nebulization, atomization or pump aerosolization of a liquid formulation, and aerosolization of a dry powder formulation, can be used in the practice of the invention. Often, the aerosolization of a liquid or a dry powder formulation will require a propellent. The propellent may be any propellant generally used in the art. Specific non-limiting examples of such useful propellants are a chlorofluorocarbon, a hydrofluorocarbon, a hydochlorofluorocarbon, or a hydrocarbon, including triflouromethane, dichlorodifluoromethane, dichlorotetrafluoroethanol, and 1,1,1,2-tetrafluoroethane, or combinations thereof.

In a particular aspect of the invention, the device for aerosolization is a metered dose inhaler. A metered dose inhaler provides a specific dosage when administered, rather than a variable dose depending on administration. Such a metered dose inhaler can be used with either a liquid or a dry powder aerosol formulation. Metered dose inhalers are well known in the art.

Once the carbohydrate or carbohydrates reach the lung by inhalation, a number of formulation-dependent factors effect the binding activity. It will be appreciated that in treating a systemic pneumococcal infection, that requires circulatory levels of the carbohydrate or carbohydrates, such factors as aerosol particle size, aerosol particle shape, the presence or absence of lung disease or emboli that may affect the absorption of the carbohydrates, pH of the lungs or the pharmaceutical carrier, etc. For each of the formulations described herein, certain lubricators, absorption enhancers, stabilizers or suspending agents may be appropriate. The choice of these additional agents will vary depending on the goal. It will be appreciated that in instances where local delivery of the carbohydrate or carbohydrates is desired or sought, such variables as absorption enhancement will be less critical.

In a further embodiment, an aerosol or parenteral formulation of the present invention can include other active ingredients in addition to the carbohydrate or carbohydrates. In a preferred embodiment, such active ingredients are those used for the treatment of lung disorders. For example, such additional active ingredients include, but are not limited to, bronchodilators, antihistamines, epinephrine, and the like, which are useful in the treatment of pulmonary conditions. In a preferred embodiment, the additional active ingredient can be an antibiotic, e.g., for the treatment of pneumonia. In a preferred embodiment, the antibiotic is pentamidine.

While in a preferred aspect the compositions of the present invention are administered in conjunction with antibiotics, it is a particular advantage of the present invention that it provides a strategy for treating antibiotic resistant pneumococcus. This is an important consideration in view of the recent increase in antibiotic resistance among virulent bacteria, a phenomenon that is of grave public health concern.

In general, the carbohydrate or carbohydrates of the present invention, are introduced into the subject in the aerosol or parenteral form in an amount between 0.01 mg per kg body weight of the mammal up to about 100 mg per kg body weight of said mammal. In a specific embodiment, the dosage is dosage per day. One of ordinary skill in the art can readily determine a volume or weight of aerosol corresponding to this dosage based on the concentration of carbohydrate or carbohydrates in an aerosol or parenteral formulation of the invention; alternatively, one can prepare an aerosol formulation which with the appropriate dosage of carbohydrate or carbohydrates in the volume to be administered, as is readily appreciated by one of ordinary skill in the art. It is also clear that the dosage will be higher in the case of inhalation therapy for a systemic pneumococcal infection, and may be lower for treating an infection of the lung only, since the local concentration of carbohydrate or carbohydrates in the lung will be much higher with pulmonary administration. It is an advantage of the present invention that administration of a carbohydrate or carbohydrates directly to the lung allows targeted drug delivery, thus limiting both cost and unwanted side effects.

The formulation may be administered in a single dose or in multiple doses depending on the severity of the infection or need for prophylaxis. For example, when administered to a subject on a respirator as protection against pneumococcal infection (a common consequence of long-term treatment on a respirator), less of the composition may be effective. If an infection commences, more of the composition can be provided to facilitate elution of adherent bacteria as well as prevent adhesion and colonization by resident bacteria. It will be appreciated by one of skill in the art the exact amount of prophylactic or therapeutic formulation to be used will depend on the stage and severity of the disease, the physical condition of the subject, and a number of other factors, which can be readily determined by the skilled physician (see, e.g., Langer et al., International Patent Publication No. WO 9403184, published Feb. 17, 1994, which is specifically incorporated herein by reference).

Systems of aerosol delivery, such as the pressurized metered dose inhaler and the dry powder inhaler are disclosed in Newman, S. P., *Aerosols and the Lung*, Clarke, S. W. and Davia, D. editors, pp. 197–22 and can be used in connection with the present invention.

Liquid Aerosol Formulations

The present invention provides liquid aerosol formulations and dosage forms for use in treating subjects suffering from or in danger of acquiring a pneumococcal infection. In general such dosage forms contain one or more carbohydrates in a pharmaceutically acceptable diluent. Pharmaceutically acceptable diluents include but are not limited to sterile water, saline, buffered saline, dextrose solution, and the like. In a specific embodiment, a diluent that may be used in the present invention or the pharmaceutical formulation of the present invention is phosphate buffered saline, or a buffered saline solution generally between the pH 7.0–8.0 range, or water.

The liquid aerosol formulation of the present invention may include, as optional ingredients, pharmaceutically acceptable carriers, diluents, solubilizing or emulsifying agents, surfactant and excipients.

The liquid aerosol formulations of the present invention will typically be used with a nebulizer. The nebulizer can be either compressed air driven or ultrasonic. Any nebulizer known in the art can be used in conjunction with the present invention such as but not limited to: Ultravent, Mallinckrodt, Inc. (St. Louis, Mo.); the Acorn II nebulizer (Marquest Medical Products, Englewood Colo.). Other nebulizers useful in conjunction with the present invention are described in U.S. Pat. Nos. 4,624,251 issued Nov. 25, 1986; 3,703,173 issued Nov. 21, 1972; 3,561,444 issued Feb. 9, 1971 and 4,635,627 issued Jan. 13, 1987.

The formulation may include a carrier. The carrier is a macromolecule which is soluble in the circulatory system and which is physiologically acceptable where physiological acceptance means that those of skill in the art would accept injection of said carrier into a patient as part of a therapeutic regime. The carrier preferably is relatively stable in the circulatory system with an acceptable plasma half life for clearance. Such macromolecules include but are not limited to Soya lecithin, oleic acid and sorbitan trioleate, with sorbitan trioleate preferred.

The formulations of the present embodiment may also include other agents useful for stabilization or for the regulation of osmotic pressure. Examples of the agents include but are not limited to salts, such as sodium chloride, or potassium chloride, and carbohydrates, such as glucose, galactose or mannose, and the like.

Aerosol Dry Powder Formulations

It is also contemplated that the present pharmaceutical formulation will be used as a dry powder inhaler formulation comprising a finely divided powder form of the carbohydrate or carbohydrates and a dispersant. The form of the carbohydrate will generally be a lyophilized powder. Lyophilized forms of carbohydrates can be obtained through standard techniques.

In another embodiment, the dry powder formulation will comprise a finely divided dry powder containing one or more carbohydrates, a dispersing agent and also a bulking agent. Bulking agents useful in conjunction with the present formulation include such agents as lactose, sorbitol, sucrose, or mannitol, in amounts that facilitate the dispersal of the powder from the device.

Diagnosis of a Pneumococcal Infection

The carbohydrates identified herein as binding to pneumococci are valuable reagents for the diagnosis of an infection with *S. pneumoniae*. Presently, diagnosis of infection with a Gram positive bacterium, including pneumococci, is difficult. Usually, diagnosis depends on a combination of symptomatology, an X-ray pattern consistent with pneumonia, and in vitro culturing of biological samples obtained from a subject suspected of having a pneumococcal infection. Such samples are typically obtained from sputum, bronchial lavage, extraction of lung fluid with a needle, and blood (which detects the presence of pneumococci that have infected blood).

According to the invention, the presence of *S. pneumoniae* in a sample from a subject suspected of having an infection with *S. pneumoniae* in can be detected by detecting binding of a carbohydrate as described above to bacteria in or from the sample. As noted above, the invention provides the unexpected discovery that pneumococci adhere to carbohydrates containing mannose linked to a disaccharide N-acetyl-D-galactosamine β1-3Gal group. Accordingly, detecting binding of this carbohydrate motif to bacteria is indicative that the bacteria are pneumococci. Furthermore, detection of binding to the GalNAcβ1-3Gal and either or both the GalNAcβ1-4Gal and the GlcNAc groups with bacteria can provide more definitive information about the identity of the bacteria as pneumococci.

According to the invention, the detection of binding of one or more of the aforementioned carbohydrate motifs can be detected independently, i.e., binding to each carbohydrate motif is detected separately. Separate detection can be accomplished by performing separate assays for each type of carbohydrate, or by using distinct labels on each carbohydrate for which binding is to be assayed. Alternatively, binding to all two or all three motifs can be detected simultaneously.

Detection of binding of carbohydrates with bacteria according to the invention can be assayed in a manner analogous to an immunoassay. In the present case, the carbohydrate acts as one binding partner, and the bacterium acts as another binding partner.

In one embodiment, a quantity of one or more carbohydrates that bind with pneumococci can be prepared and optionally labeled, such as with an enzyme, a compound that fluoresces and/or a radioactive element, and may then be introduced into a tissue or fluid sample of a mammal believed to be infected with pneumococci. After the labeled material has had an opportunity to react with sites within the tissue, the resulting mass may be examined by known techniques, which may vary with the nature of the label attached. Preferably if such in vivo detection is desired, the radio-label is technetium-99 ($^{99}Tc$), or a magnetic shift reagent label such as gadolinium or manganese, is used as a label.

The presence of pneumococci in animals can be ascertained in general by immunological procedures, which utilize one or more carbohydrate binding partner to pneumococci, in which one component is labeled with a detectable label. In a preferred aspect, the presence of pneumococci is ascertained in an assay that involves a carbohydrate labeled with a detectable label. In a specific aspect, the detectable label may be the binding partner of another reagent, e.g., biotin (which binds with avidin or streptavidin), or an antigen for an antibody. The procedures may be summarized by the following equations wherein the asterisk indicates that the molecular species is labeled, and "C" in this instance stands for the carbohydrate or carbohydrates, and "B" stands for the bacterium:

A. $C^* + B + C = C^*B$

B. $C_1 + C_2^* + B = C_1 B C_2^*$

These general procedures and their application are all familiar to those skilled in the art and are presented herein as illustrative and not restrictive of procedures that may be utilized within the scope of the present invention. An immunoassay procedure analogous to the "competitive" procedure, Procedure A, is described in U.S. Pat. Nos. 3,654,090 and 3,850,752. An immunoassay analogous to procedure B, the "sandwich" procedure, is described in U.S. Pat. Nos. RE 31,006 and 4,016,043.

A further alternate diagnostic procedure employs multiple labeled compounds in a single solution for simultaneous radio-assay. In this procedure, analogous to the procedure disclosed in U.S. Pat. No. 4,762,028 to Olson, a composition may be prepared with two or more carbohydrate molecules in a coordinated compound having the formula: radioisotope-chelator-carbohydrate molecule.

The labels most commonly employed for these studies are radioactive elements, enzymes, chemicals which fluoresce when exposed to ultraviolet light, and others.

Suitable radioactive elements may be selected from the group consisting of $^3H$, $^{14}C$, $^{32}P$, $^{35}S$, $^{36}Cl$, $^{51}Cr$, $^{57}Co$, $^{59}Fe$, $^{90}Y$, $^{125}I$, $^{131}I$, and $^{186}Re$. In the instance where a radioactive label, such as one of the isotopes listed above, is used, known currently available counting procedures may be utilized to detect or quantitate the amount of label, and thus the amount of material bound.

In the instance where the label is an enzyme, detection may be accomplished by any of the presently utilized colorimetric, spectrophotometric, fluorospectrophotometric, thermometric, amperometric or gasometric techniques known in the art. The enzyme may be conjugated to the carbohydrate, by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase, hexokinase plus GDPase, RNAse, glucose oxidase plus alkaline phosphatase, NAD oxidoreductase plus luciferase, phosphofructokinase plus phosphoenol pyruvate carboxylase, aspartate aminotransferase plus phosphoenol pyruvate decarboxylase, and alkaline phosphatase. U.S. Pat. Nos. 3,654,090; 3,850,752; and 4,016,043 are referred to by way of example for their disclosure of alternative labeling material and methods.

A number of fluorescent materials are known and can be utilized as labels. These include, for example, fluorescein, rhodamine and auramine.

Various assay formats are also contemplated by the present invention for detecting the presence, and if desired, the amount, of pneumococcal bacteria in a sample. For example, a direct "sandwich"-type ELISA can be performed, in which one carbohydrate is attached to the solid phase support, and a labeled carbohydrate (which may share the same motif as the first, or which may have one of the other motifs) is used to detect binding of bacteria to the solid phase carbohydrate.

The present invention includes assay systems that may be prepared in the form of test kits for the quantitative analysis of the extent of the presence of pneumococcal bacteria. The system or test kit may comprise a labeled component, e.g., prepared by one of the radioactive and/or enzymatic techniques discussed herein, coupling a label to a carbohydrate binding partner of pneumococci. Alternatively, a test kit of the invention may comprise such a carbohydrate associated with or capable of being associated with a solid phase support, including but not limited to, a microtiter plate, chromatography beads (SEPHAROSE and the like), and cells (for rosetting experiments).

In a further embodiment of this invention, commercial test kits suitable for use by a medical specialist may be prepared to determine the presence or absence of pneumococci. Such kits can also be used to determine the amount of pneumococci in a sample. In accordance with the testing techniques discussed above, one class of such kits will contain at means for detecting binding of a carbohydrate as described herein and a pneumococcus, and may include directions, depending upon the method selected. The kits may also contain peripheral reagents such as buffers, stabilizers, etc.

For example, a first assay format contemplates a bound carbohydrate to which is added the biological sample suspected of containing pneumococci, followed by a labeled carbohydrate (or anti-pneumococci antibody). The resulting substrate is then washed, after which detection proceeds by the measurement of the amount of label specifically retained on the solid phase.

All of the protocols disclosed herein may be applied to the qualitative and quantitative determination of pneumococci and to the concomitant diagnosis and surveillance of *S. pneumoniae* infection.

The present invention will be better understood from a review of the following illustrative description presenting the details of the constructs and procedures that were followed in its development and validation.

EXAMPLE: RECEPTOR SPECIFICITY OF ADHERENCE OF *STREPTOCOCCUS PNEUMONIAE*

The adherence of *S. pneumoniae* to human type II pneumocytes and endothelial cells is critical to the pathogenesis of pneumococcal pneumonia and bacteremia. This example demonstrates that the preferred target cell to which pneumococci adhere in the lung is the type II lung cell and reports an in vitro adherence assay to determine the molecular details of this interaction. Pneumococcal receptors on cultured human lung cells (LC) and endothelial cells (EC) appeared to be glycoproteins, since treatment of the monolayers with tunicamycin (an inhibitor of glycosylation) significantly impaired bacterial adherence.

Inhibition of adherence to LC and EC occurred following incubation with several carbohydrates including, GalNAc, mannose and GalNAcβ1-4Gal- and GalNAcβ1-3Gal-containing glycoconjugates. Pneumococci could bind directly to these immobilized sugars and their addition to adherent pneumococci could elute the bacteria from LC and EC. Combinations of glycoconjugates indicated that two independent classes of pneumococcal receptor existed on both cell types. These were defined by the minimal receptor units GalNAcβ1-4Gal and GalNAcβ1-3Gal which participate in pneumococcal cell wall and protein-dependent mechanisms of adherence, respectively.

Materials and Methods

Bacterial strains and cultivation conditions. *S. pneumoniae* strains of serotype 2 (AII and D39) and serotypes 18C, 9V, and the unencapsulated strain R6 (isogenic with D39 and AII) were grown on trypticase soy agar (Difco, Detroit, Mich.) containing 3% sheep blood (Micropure Medical Inc., Stillwater, Mich.) for 18 h at 37° C. Bacteria were harvested from the plate into 1 ml Dulbecco's phosphate buffered saline (DPBS; Whittaker Bioproducts, Watersville, Md.) and labelled with fluorescein isothiocyanate (FITC 1 mg/ml; Sigma Chemical Company, St. Louis, Mo.) dissolved in a buffer containing 0.05M sodium carbonate and 0.1M sodium chloride as previously described (Geelen et al., 1993, Infect. Immun. 61:1538). The bacteria were washed twice by centrifugation (3,000 rpm, 3 min), resuspended in 1 ml albumin buffer (Geelen et al., supra) and diluted to between $10^5$ and $10^{10}$ cfu/ml. For some experiments, R6 pneumococci were grown in defined medium with either choline or ethanolamine as the aminoalcohol (Tuomanen et al., 1985, J. Infect. Dis. 151:859).

Pneumococcal cell wall preparation. Purified whole cell wall from R6 was prepared as previously described (Geelen et al., supra). Briefly, logarithmically growing pneumococci were heat-killed and crude cell wall extracted in 5% sodium dodecyl sulfate (SDS; 100° C., 30 min). SDS was removed by washing and the cell wall treated with DNase, RNase and trypsin. After reprecipitation in boiling SDS, the walls were washed, lyophilized, and stored at room temperature. For use in bioassays, pneumococcal cell wall suspensions were homogenized by sonification with a Branson Sonifier (model 2200; Branson Ultrasonic Corp., Danbury, Conn.) and resuspended to a final concentration of 50–100 mg/ml in albumin buffer.

These concentrations were chosen as they had previously been shown to produce maximum inhibition of pneumococcal adherence to human endothelial cells (Geelen et al., supra).

Rabbit mixed and type II lung cell preparations. Rabbit mixed and type II lung cells were prepared as previously described (Dobbs and Mason, 1979, J. Clin. Invest. 63:378). Briefly, lungs were minced and digested with collagenase, elastase and DNase for 60 min at 37° C. Large pieces were removed using a gauze filter and cells were pelleted and washed twice. The resulting mixed lung cells were resuspended in 20 ml of calcium-containing buffer with 0.5% albumin to a density of $10^4$/ml. To purify alveolar type II cells from the mixed lung cell suspension, the mixture was layered on an albumin gradient of 10 ml 16.5 g % over 10 ml 35 g % and centrifuged at 1200 rpm for 20 min at 4° C. The top 26 ml of the gradient was discarded and cells in the next 12 ml were harvested, washed and adjusted to a concentration of $10^4$/ml.

Cell viability was >90% as assessed by trypan blue exclusion and >80% of the cells contained osmiophilic lamellar bodies typical of type II lung cells when examined by electron microscopy.

Human type II pneumocytes and vascular endothelial cells. The human type II lung cell line A549 (LC; American type culture collection) was added to tissue culture flasks coated with gelatin (0.2%) and cultured in Nutrient mixture F12 Ham medium (Sigma) supplemented with 10% fetal calf serum (Sigma). Primary cultures of human umbilical vein endothelial cells (EC; passage 1, Clonetics Corp., San Diego, Calif.) were added to tissue culture flasks coated with fibronectin (50 µg/ml) and grown in Medium 199 (Sigma) supplemented as previously described (Krivan et al., 1988, Proc. Natl. Acad. Sci. USA 85:6157). In order to determine the influence of glycosylation of proteins on pneumococcal adherence to LC and EC, some monolayers were prepared from cells grown for 96 h at 37° C. in the presence of tunicamycin (0.55 µg/ml; Sigma) (Dobbs and Mason 1979, J. Clin. Invest. 63:378). At confluence the cells were prepared for subculture with trypsin-0.05% EDTA (Sigma). For adherence assays, cells were transferred to Terasaki 60-well culture dishes (Robbins Scientific, Sunnyvale, Calif.) coated with fibronectin (50 mg/ml) and cultured for another 24 to 48 h to form a confluent monolayer.

Prior to the adherence assay, culture fluid was removed by washing the monolayers twice with medium 199 (Sigma).

Adherence of bacteria to primary rabbit mixed lung cells. To study adherence of pneumococci to primary rabbit mixed lung cells and type II pneumocytes, AII or R6 ($10^3$–$10^9$ cfu/ml) were added to $10^4$ lung cells in a 1 ml volume and incubated under rotation for 30 min at 37° C. Lung cells were then separated from non-adherent bacteria by washing six times by centrifugation (270 g, 5 min) and resuspension in medium 199. Bacteria adherent to the final cell pellet were then enumerated both by plating and visualization by Gram stain and the baseline established from six independent experiments. These quantitation techniques were chosen to ensure that adherence reflected viable bacteria without the potential complications of a bacterial surface derivatized with a detection label. Subsequent comparison of the adherence of killed bacteria and fluorescein labelled bacteria to the adherence of viable cells indicated no significant differences (see below).

Adherence of pneumococci to cultured human LC and EC. Adherence of pneumococci to LC and EC was investigated using the protocol previously described for cultures of human vein endothelial cells (Geelen et al., 1993, Infect. Immun. 61:1538). FITC-labelled bacteria ($10^5$ to $10^8$ cfu/ml; 10 μl/well) were incubated with cell monolayers for up to 150 min at 37° C. Pneumococcal adherence was also assessed at 4° C.

Nonadherent bacteria were removed by washing the monolayers 5 times with medium 199 and the cells were then fixed in 2.5% glutaraldehyde. Adherent pneumococci were counted visually with an inverted microscope (Diaphot-TMD; Nikon Inc., Melville, N.Y.) equipped for fluorescence with an IF DM-510 filter. Adherence was expressed as the number of attached bacteria per 100 eukaryotic cells counted in a 40× field. Values for two wells were averaged and each experiment was performed on at least six separate occasions. Inter-and-intra assay coefficients of variation of the adherence assay were found to be 18% and 15% respectively.

To test the ability of pneumococcal cell wall to inhibit adherence, cultured LC and EC were incubated with cell wall (5 μl; 50 or 100 μg/ml) for 30 min at 37° C. before the addition of labelled bacteria. For experiments to define the ability of carbohydrates to inhibit adherence, FITC-labelled R6 ($2 \times 10^7$ cfu/ml) were pre-incubated for 15 min at room temperature (Tuomanen et al., 1988, J. Exp. Med. 168:267) with final concentrations of one of the following as listed in Table 1: monosaccharides at between 1 and 50 mM, glycoconjugates at 0.002–2 mM (Sigma), or albumin buffer without glucose (control).

Bacteria were centrifuged (3,000 rpm, 3 min) to remove the sugar, resuspended to $1 \times 10^7$ cfu/ml in albumin buffer and added to the adherence assay. Adherence was assessed after 30 min at 37° C. of co-incubation of R6 and the LC or EC monolayers. Results were expressed as the number of bacteria attaching to a designated sugar. This value is derived from the difference between adherence in the absence or sugar (control wells) and the presence of sugar. For example, if 100 bacteria adhere in control wells and 60 bacteria adhere when sugar A is added, then it is calculated that 40 bacteria (40%) adhere to cells in a manner dependent on sugar A.

Adherence of pneumococci to immobilized glycoconjugates. Solid-phase binding assays were carried out according to Lee and colleagues (Lee, et al., 1994, Mol. Microbiol. 11:705). Stock solutions of the monosaccharides (100 mM) and complex carbohydrates (2 mM) were prepared in 10% chloroform in methanol (v/v). Dilutions of the monosaccharides (12–50 mM) and complex carbohydrates (0.004–0.4 mM) were made in methanol.

Terasaki 60-well culture dishes (Robbins Scientific, Sunnyvale, Calif.) were coated with 10 μl per well of either the monosaccharides or glycoconjugates in methanol, or methanol as control, and allowed to evaporate to dryness in at 4° C. The wells of the microtitre plate were then blocked by incubation (1 h, 37° C.) with 5% (w/v) bovine serum albumin (BSA; Sigma) in phosphate buffered saline (PBS), pH 7.4.

The excess BSA was decanted and the wells washed once with 0.05% BSA in PBS. Fluorescein labelled pneumococci ($10^7$ cfu/ml) were allowed to adhere to the plates for 30 min at 37° C. and adherence quantified visually using an inverted fluorescence microscope.

Statistics. Differences between groups were tested by the Wilcoxon signed ranks test. All results are expressed as means and standard deviations of at least six experiments.

Results

Interaction of Pneumococci with Lung Cells

Figure 1B:
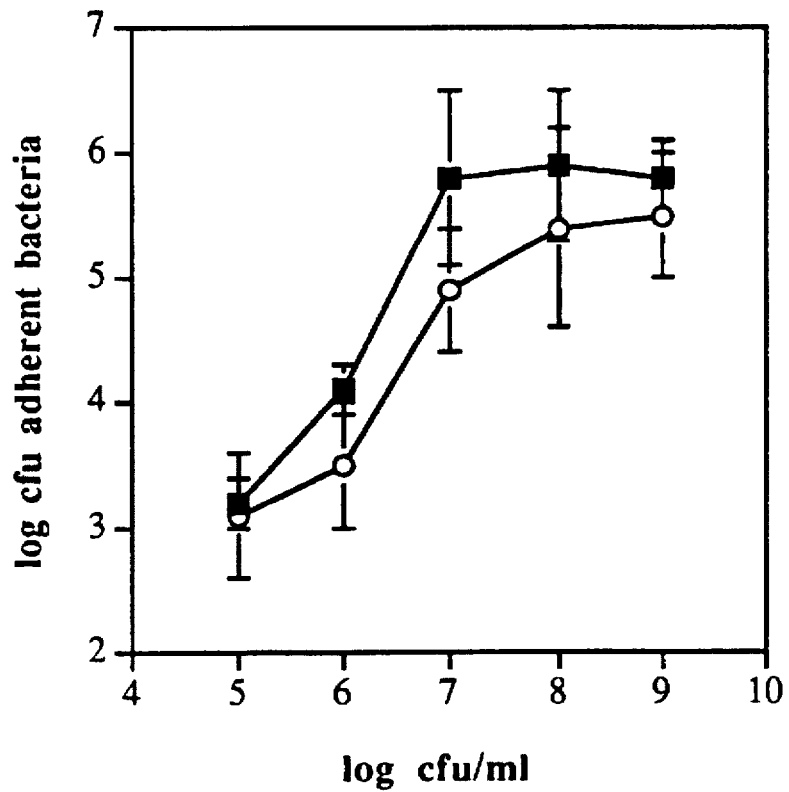

Adherence of pneumocci to primary lung cells. Adherence of encapsulated AII pneumococci to mixed rabbit lung cells was concentration dependent and saturable (FIG. 1A). Adherence to purified type II lung cells was consistently 10–100 fold greater at each inoculum than to mixed lung cells suggesting the type II lung cell was the preferred target. At the maximum level of adherence, $10^5$ cfu were associated with $10^4$ type II cells indicating an adherence index of ~10 pneumococci per cell. Adherence to purified type II cells was equivalent for encapsulated AII and isogenic unencapsulated R6 suggesting that the capsule did not affect pneumococcal attachment (FIG. 1B).

Figure 2A:
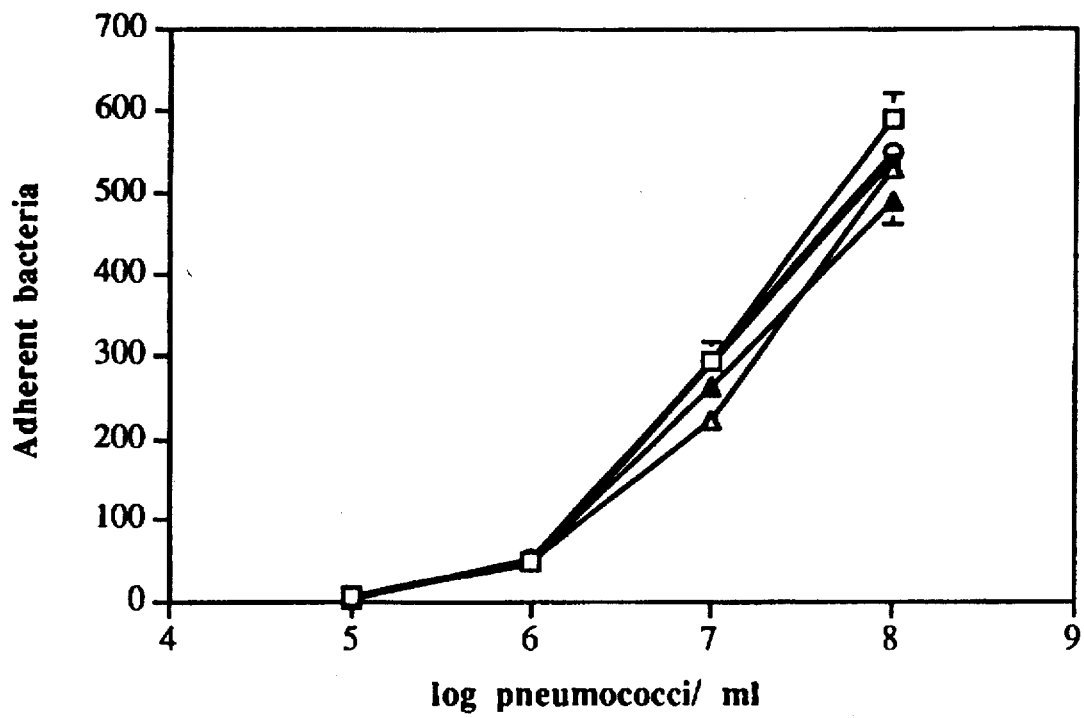
Figure 2B:
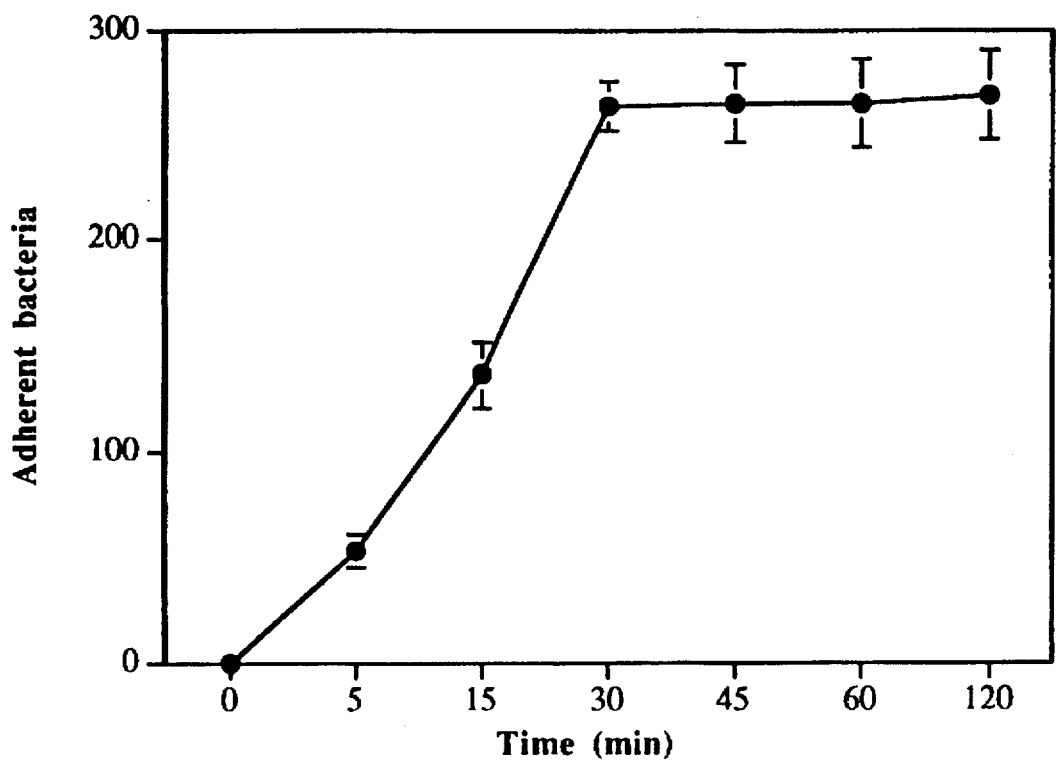

Adherence of R6, AII, D39, 9V and 18C to human type II lung cell line. A model of pneumococcal adherence to type II pneumocytes was developed using the A549 type II LC line. Encapsulated strains AII, D39, 9V and 18C and the unencapsulated R6 adhered in a dose-dependent fashion (FIG. 2A). A threshold dose of approximately $10^6$ cfu/ml was required to detect attachment. With higher concentrations, adherence increased in a linear fashion to >10 bacteria per cell, a value similar to the maximum for primary type II cells. The attachment of pneumococci to LC reached a plateau within 45 min (FIG. 2B). To investigate whether active metabolism was required for adherence, live and heat-killed R6 (10 min, 60° C.) were compared in the adherence assay. At an input concentration of $10^7$ cfu/ml, the number of attached bacteria per 100 LC was 296±10 and 273±14 (p>0.05) for live and heat-killed R6, respectively.

Role of pneumococcal cell wall in adherence of R6 to human LC. Pretreatment of type II LC monolayers (30 min, 37° C.) with purified pneumococcal cell wall (50 μg/ml) significantly (p<0.05) decreased the adherence of $10^5$, $10^6$ and $10^7$ cfu/ml of R6 to LC by 39±12%, 47±17% and 57±7%, respectively. Similar results were obtained using 100 μg/ml of pneumococcal cell wall (data not shown). To directly assess the role of the phosphorylcholine moiety present in the cell wall teichoic acid in adherence, pneumococci were cultured in medium containing ethanolamine, which biosynthetically substitutes the aminoalcohol in the teichoic acid. At an input concentration of $10^7$ cfu/ml, the number of R6 adherent to 100 LC was 273±14 and 294±14 (p>0.05) for pneumococci grown with choline and ethanolamine, respectively.

Receptor Specificity for Pneumococci on LC and EC

Effect of tunicamycin on pneumococcal adherence. Tunicamycin inhibits the glycosylation of cell surface 7 glycoproteins by blocking the first step in the biosynthetic pathway of the oligosaccharide portion of asparagine-linked high-mannose- and complex-type glycoproteins (Hranitzky et al., 1985, Infect. Immun. 49:336). Adherence of pneumococci to monolayers treated with tunicamycin was significantly (p<0.05) impaired compared with untreated monolayers. At an input concentration of $10^7$ cfu/ml of R6, the number of pneumococci adherent to 100 cells was 67±9 and 240±15 for EC cultured in the presence and absence of tunicamycin. Similar results were obtained for LC.

The carbohydrate specificity of the receptor(s) for pneumococcus on human LC and EC. The minimal receptor unit was defined using competition assays in which simple and complex carbohydrates were used to interfere with S. pneumoniae strain R6 adherence to human LC and EC. Comparison of the ability of monosaccharides to inhibit adherence indicated that N-acetyl-D-galactosamine (GalNAc) and D-mannose played a role in >40% of the pneumococcal adherence to EC and LC; D-galactose was an additional specificity on EC only (Table 1). Since the pattern of competitive inhibition by monosaccharides does not necessarily predict the structure of a receptor (Lee et al., 1994, Mol. Microbiol. 11:705), the ability of a library of glycoconjugates containing mannose or N-acetyl-D-galactosamine to inhibit adherence was tested. The two mannose disaccharides mannose-D-mannose and methyl D-mannoside were effective receptor analogs for R6 adherence to both LC and EC (Table 1). Substitution of the terminal D-mannoside with D-galactoside led to a complete loss of activity of the molecule (Table 1).

was inactive at all concentrations investigated (0.003–2 mM). This suggested that receptor activity was associated with the presence of GalNAc linked to Gal by either a β1,4 linkage (asialo-GM2) or a β1,3 linkage (globoside). Reversal of the positions of GalNAc and Gal, as in the disaccharide Galβ1-3GalNAc (2-ADGG) rendered the carbohydrate inactive.

Figure 3A:
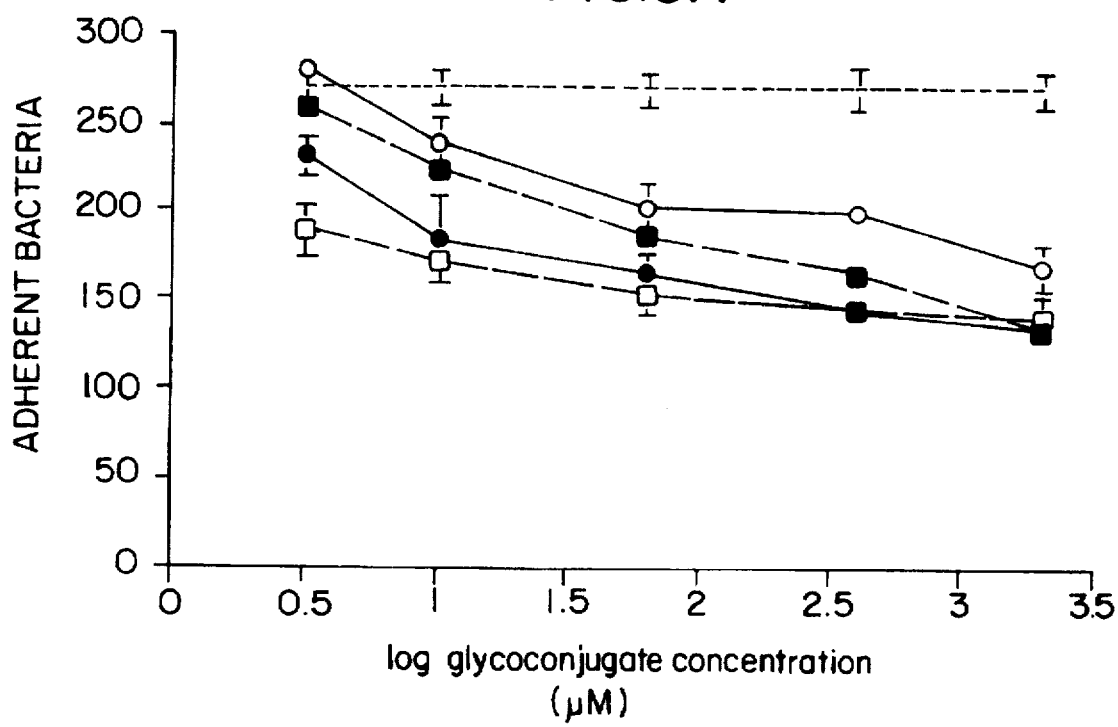
Figure 3B:
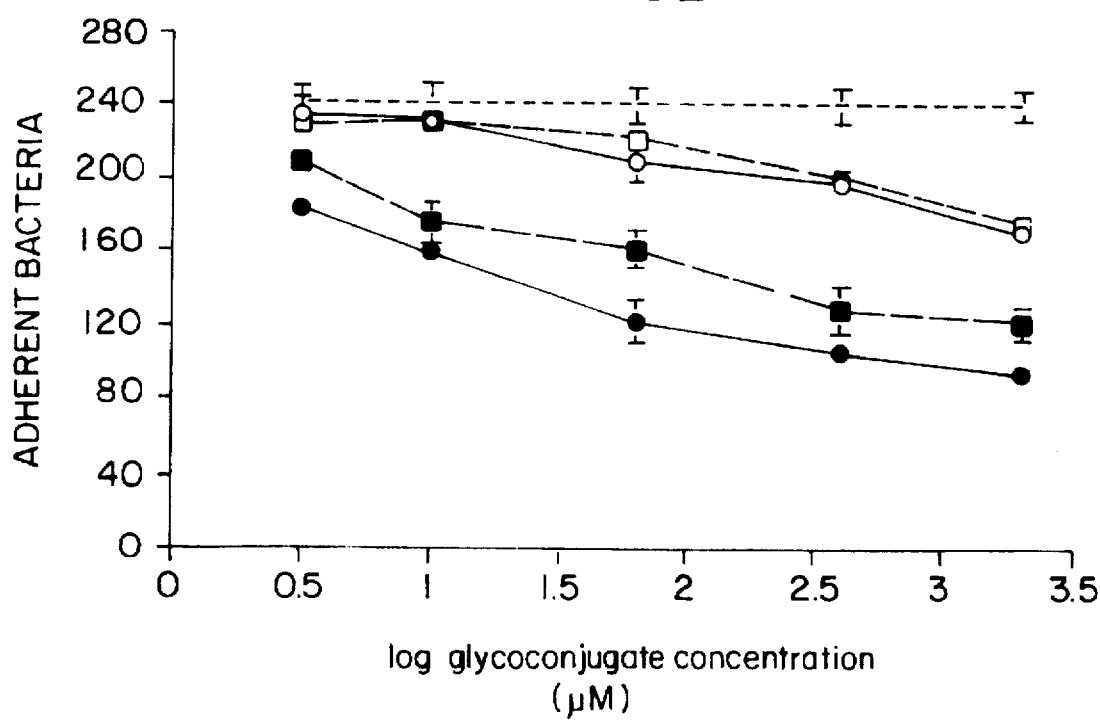

A variety of GalNAc-β1,4-Gal-containing sugars were compared to determine how substitutions affected the potency of the β1,4 linkage active in asialo GM-2. Addition of a terminal Gal to create asialo-GM-1 decreased the ability to serve as a receptor by ~10-fold for LC (half maximal inhibition occurred at $10^2$ μM for asialo GM-2 and at $10^3$ μM for asialo GM-1) and >100 fold for EC (half maximal inhibition was not reached at >$10^3$ μM for asialo GM-1) (FIGS. 3A and 3B). The small effect of asialo GM-1 on LC was virtually eliminated by substitution with sialic acid (monosialo-GM-1) (Table 1).

A similar analysis for the effect of substitutions on the activity of the β1-3 linkage produced different results for LC and EC. Addition of a terminal GalNAc to globoside (forssman glycolipid) decreased receptor activity on EC 25 fold (FIG. 3B). In contrast, forssman glycolipid showed a substantially increased activity over globoside for LC in that the concentration range over which a reduction in R6 adherence could be detected was greater, although the same maximal inhibition of R6 adherence occurred (~52%) (FIG. 3A).

TABLE 1

Antiadherence Activity of Monosaccharides and Glycoconjugates

| Monosaccharide/Glycoconjugate | Carbohydrate Specificity# | Number of Pneumococci Adherent to Designated Sugar on Host Cell of total)* | |
|---|---|---|---|
| | | Lung Cell | Endothelial Cells |
| Control | | 270 ± 10 | 240 ± 15 |
| Monosaccharides (50 mM) | | | |
| D-galactose | Gal | 10 ± 2 (4%) | 112 ± 6 (47%) |
| D-glucose | Glc | 5 ± 4 (2%) | 11 ±]8 (5%) |
| L-fucose | | 8 ± 3 (3%) | 19 ± 15 (8%) |
| Sialic Acid | | 6 ± 4 (2%) | 13 ± 6 (5%) |
| D-mannose | | 142 ± 11 (53%) | 110 ± 6 (46%) |
| N-acetyl-D-galactosamine | GalNAc | 137 ± 7 (51%) | 108 ± 9 (55%) |
| N-acetyl-D-glucosamine | GlcNAc | 5 ± 2 (2%) | 18 ± 6 (8%) |
| Glycoconjugates (2 mM) | | | |
| Mannose-D-mannose | α-D-man[1–3]D-man | 121 ± 9 (45%) | 146 ± 4 (61%) |
| Methyl-α-D-mannopyranoside | | 137 ± 17 (51%) | 150 ± 6 (63%) |
| Methyl-α-D-galactopyranoside | | 18 ± 4 (7%) | 49 ± 11 (20%) |
| 2-ADGG | Galβ1-3GalNAc | 6 ± 3 (2%) | 11 ± 3 (5%) |
| Lactose | Galβ1-4Glc | 11 ± 3 (4%) | 66 ± 11 (28%) |
| Lactosylceramide | Galβ1-4Glcβ1-1Cer | 5 ± 2 (2%) | 7 ± 5 (3%) |
| Asialo-GM1 | Galβ1-3GalNAcβ1-4Galβ1-4Glcβ1-1Cer | 100 ± 13 (37%) | 70 ± 9 (29%) |
| Asialo-GM2 | GalNAcβ1-4Galβ1-4Glcβ1-1Cer | 140 ± 9 (52%) | 140 ± 4 (58%) |
| Monosialo-GM1 | Galβ1-3GalNAcβ1-4(NeuAcα2-3)Galβ1-4Glcβ1-1Cer | 42 ± 8 (16%) | 4 ± 2 (2%) |
| Forssman Glycolipid | GalNAcα1-3GalNAcβ1-3Galα1-4Galβ1-4Glcβ1-1Cer | 130 ± 7 (51%) | 70 ± 12 (29%) |
| Globoside | GalNAcβ1-3Galα1-4Galβ1-4Glcβ1-1Cer | 140 ± 9 (52%) | 110 ± 8 (47%) |

Gal = galactose, Glc = glucose, GalNac = N-acetyl-d-galactosamine, GlcNAc = N-acetyl-d-glucosamine, 2-ADGG = 2-acetamido-2-deoxy-3-O-B-D-galactopyranosyl-d-galactopyranose, Man-D-Man = 3-O-A-D-Mannopyranosyl-d-mannopyranose, and Cer = ceramide.
*Number of pneumococci adherent to sugar = bacterial adherence to 100 host cells in absence of sugar - bacterial adherence to 100 host cells in presence of sugar.
Values given are means ± SD of six independent experiments.

Figure 4A:
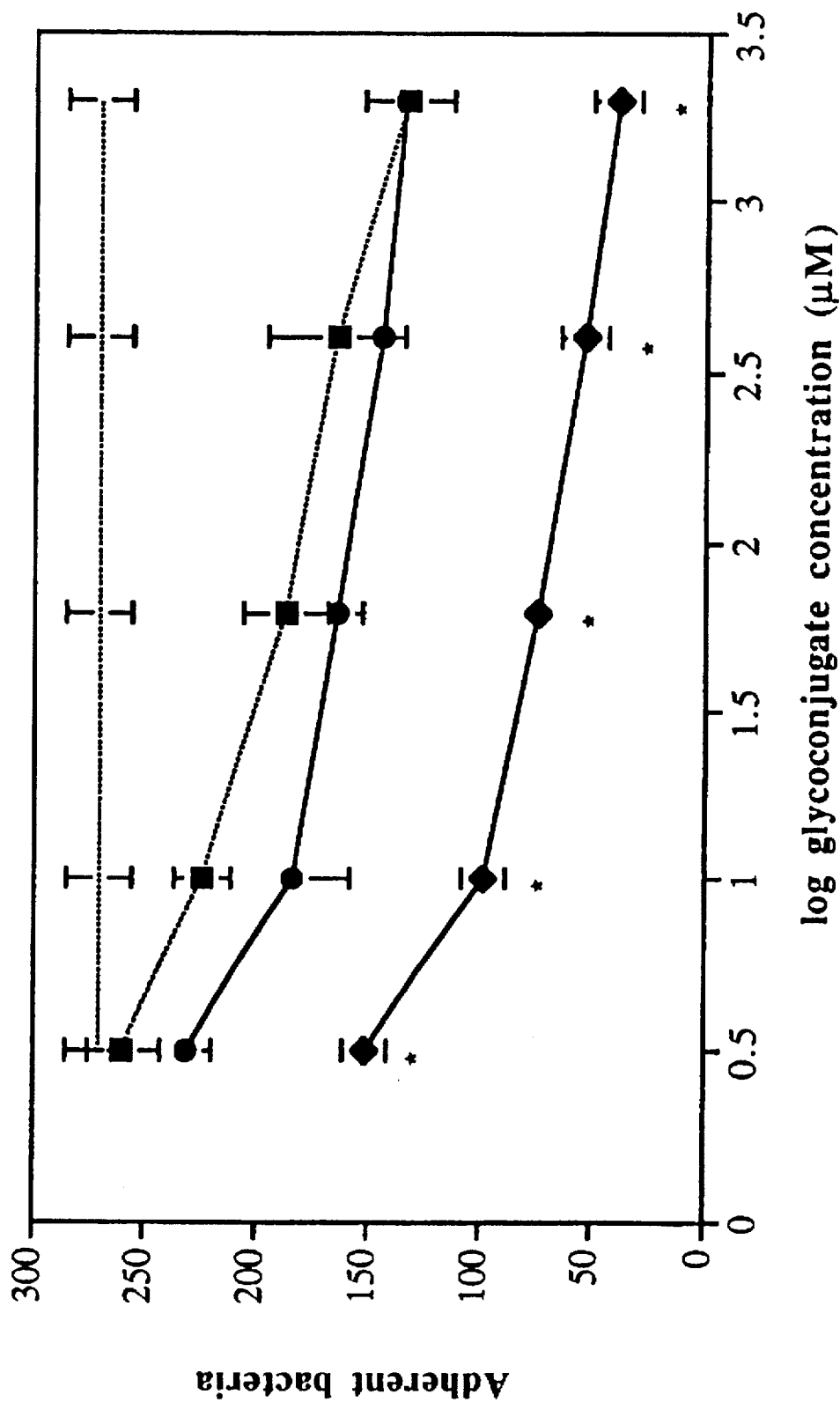
Figure 4B:
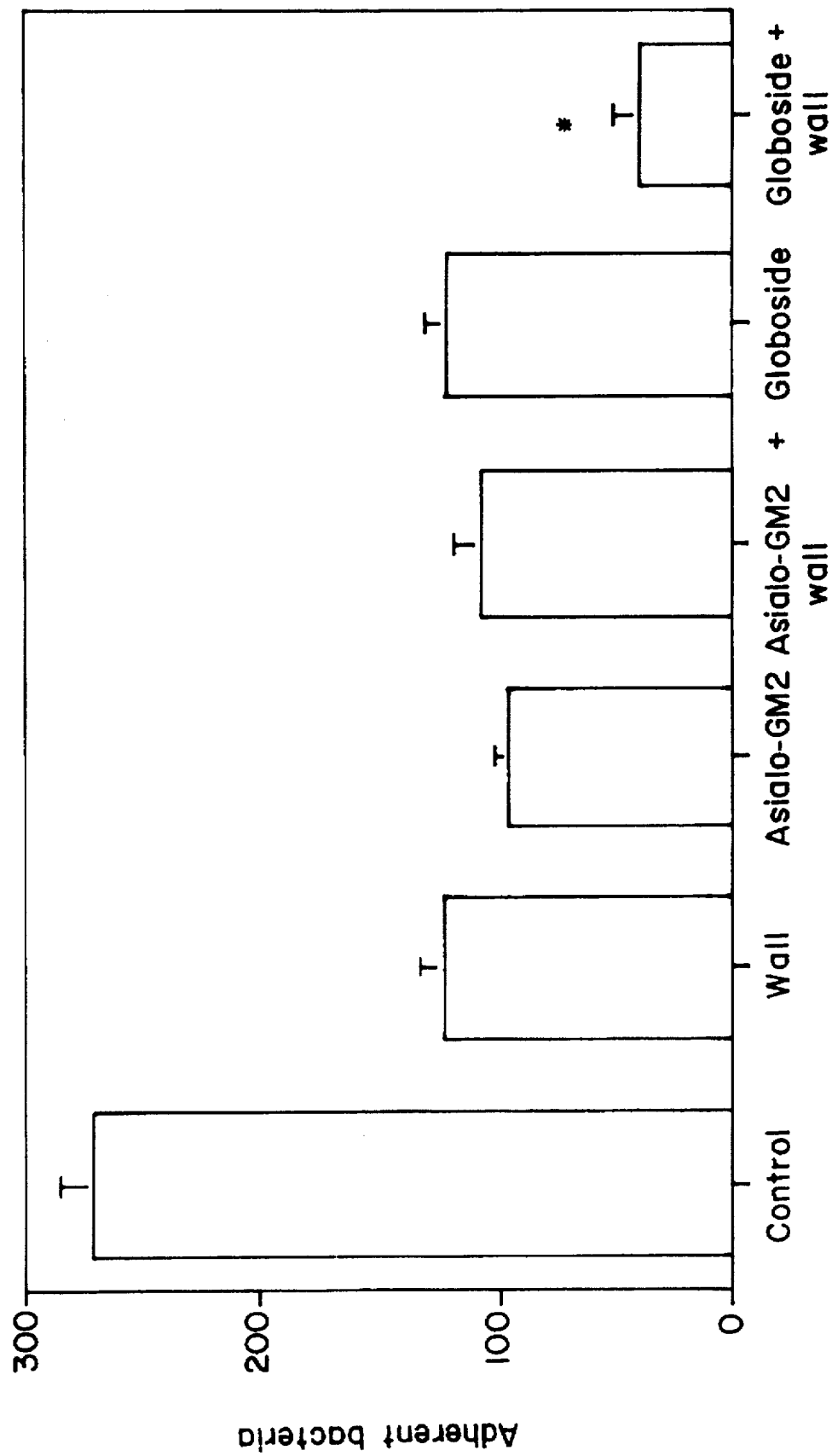

Of the complex GalNAc-containing carbohydrates tested, two were found to be highly effective targets of adherence on both LC and EC: asialo-GM2 and globoside (Table 1). The lactosylceramide (GalNAcβ1-4Glc1-1Cer) group representing the common core of both of these glycoconjugates To investigate whether the carbohydrate specificities identified in Table 1 and FIG. 3 were contained in one or multiple receptors, combinations of sugars were tested looking for additive effects indicative of two independent receptor specificities. Two component mixtures were prepared containing concentrations which separately produced maximal inhibitory effects on R6 adherence. The results of these studies are shown in Table 2. Mannose was not found to be additive with any other sugar or glycoconjugate suggesting it was a component of each class of receptors. A combination of asialo-GM1 plus asialo-GM2 or forssman glycolipid plus globoside was not additive in either cell type. A significant additive effect, virtually eliminating pneumococcal adherence, was seen with a combination of asialo-GM2 and globoside for both EC and LC (FIG. 4A). These results suggested that the β1,4 and β1,3 linked GalNAc-Gal were distinct receptors. This was further supported by the ability of purified pneumococcal cell wall to further decrease adherence in the presence of globoside from ~50% to 20% of control values while having no demonstrable additive effect to that of asialo-GM2 (FIG. 4B).

TABLE 2

Effect of Combinations of Sugars on Pneumococcal Adherence to Cultured Human Lung and Endothelial Cells

| Monosaccharide/ Glycoconjugate# | Number of Pneumococci Adherent to Designated Sugar on Host Cell¶ | |
| --- | --- | --- |
| | Lung Cells | Endothelial Cells |
| Control | 270 ± 10 | 240 ± 15 |
| Monosaccharides (50 mM) | | |
| GalNAc | 137 ± 7 | 108 ± 9 |
| Gal | 10 ± 2 | 112 ± 6 |
| D-Mannose | 142 ± 11 | 110 ± 6 |
| GalNAc + Gal | NT | 120 ± 11 |
| GalNAc + Man | 141 ± 8 | 115 ± 8 |
| Gal + Man | NT | 117 ± 7 |
| Glycoconjugates (2 Mm) | | |
| Asialo-GM1 | 100 ± 13 | 70 ± 9 |
| Asialo-GM2 | 140 ± 9 | 140 ± 4 |
| Globoside | 140 ± 9 | 110 ± 8 |
| Forssman | 130 ± 7 | 70 ± 12 |
| Man-man | 121 ± 9 | 146 ± 4 |
| Asialo-GM2 + asialo-GM1 | 139 ± 11 | 142 ± 7 |
| Globoside + forssman | 134 ± 6 | 108 ± 10 |
| Asialo-GM2 + globoside | 64 ± 9* | 40 ± 8* |

TABLE 2-continued

Effect of Combinations of Sugars on Pneumococcal Adherence to Cultured Human Lung and Endothelial Cells

| Monosaccharide/ Glycoconjugate# | Number of Pneumococci Adherent to Designated Sugar on Host Cell¶ | |
| --- | --- | --- |
| | Lung Cells | Endothelial Cells |
| Man-man + asialo-GM2 | 142 ± 5 | 147 ± 6 |
| Man-man + globoside | 143 ± 8 | 150 ± 4 |

GalNAc = N-acetyl-D-galactosamine,
Gal = galactose,
Man = mannose.
NT = not tested.
R6 incubated (15 min., room temp.) with sugar, centrifuged and co-incubated with monolayers (30 min. at 37° C.). Final concentration indicated was composed of single sugar or equally of the 2 sugars tested.
*p < 0.05 compared to single sugar alone.
¶Bacterial adherence to 100 cells in absence of sugar - bacterial adherence to 100 cells in presence of sugar. Values given in the table are mans ± SD of 6 experiments.

Receptor analogs with sufficient binding affinity can effectively compete with the host cell receptor so as to cause elution of bacteria. GalNAc or D-mannose (50 mM) eluted 65±10% and 64±8%, respectively, of the adherent bacteria on LC within 60 min. Similar results for GalNAc (58±9%) and D-mannose (68±7%) were obtained with EC. More effective elution of adherent pneumococci occurred following incubation of LC or EC with asialo-GM2 (80 μM; 75±8% and 70±7%, respectively) or globoside (80 μM; 79±10% and 63±5%, respectively). Virtually all bacteria (>95%) were eluted from either cell type by a combination of 80 μM each of globoside and asialo-GM2.

Direct adherence of pneumococci to immobilized carbohydrates. Consistent with the receptor analog activity demonstrated in adherence assays using eukaryotic cells, pneumococci were able to adhere directly to immobilized Gal, GalNAc, GlcNAc, mannose, asialo-GM1, asialo-GM2, forssman glycolipid and globoside (Table 3).

Pneumococcal adherence was greatest to asialo-GM2 and asialo-GM1, followed at 10-fold less to forssman glycolipid or globoside. Adherence to simple sugars was approximately 100-fold less than to glycoconjugates.

TABLE 3

Direct Adherence of Pneumococci to Immobilized Carbohydrates

| Monosaccharide/ Disaccharide | Adherent Bacteria# | | | Glycoconjugate | Adherent Bacteria# | | |
| --- | --- | --- | --- | --- | --- | --- | --- |
| | 50 mM | 25 mM | 12.5 mM | | 0.4 mM | 0.07 mM | 0.04 Mm |
| Gal | 79 ± 6* | 55 ± 5* | 36 ± 7 | Asialo-GM1 | 558 ± 21* | 406 ± 19* | 86 ± 10* |
| GalNAc | 103 ± 10* | 65 ± 8* | 38 ± 9 | Asialo-GM2 | 601 ± 18* | 439 ± 24* | 94 ± 11* |
| Glc | 35 ± 4 | 30 ± 6 | 32 ± 5 | Globoside | 302 ± 27* | 101 ± 13* | 64 ± 9* |
| GlcNAc | 95 ± 4* | 66 ± 2* | 36 ± 4 | Forssman Glycolipid | 118 ± 20* | 94 ± 7* | 76 ± 8* |
| Fucose | 36 ± 12 | 33 ± 4 | 35 ± 8 | Lactosylceramide | 45 ± 8 | 43 ± 4 | 40 ± 6 |
| Mannose | 99 ± 11* | 75 ± 8* | 38 ± 9 | | | | |
| Sialic Acid | 38 ± 9 | 41 ± 3 | 40 ± 4 | | | | |
| Lactose | 61 ± 2* | 39 ± 5 | 39 ± 7 | | | | |
| 2-ADGG | 37 ± 9 | 41 ± 8 | 40 ± 4 | | | | |

Gal = galactose, GalNAc = N-acetyl-d-galactosamine, Glc = Glucose, GlcNac = N-acetyl-d-glucosamine and 2-ADGG = 2-acetamido-2-deoxy-3-O-B-D-galactopyranosyl-d-galactopyranose.
Pneumococci ($10^7$ cfu/ml) were incubated with immobilized simple sugars (12.5–50 Mm) or glycoconjugates (0.04–0.4 mM) for 30 min. at 37° C. and the number of adherent bacteria in 100× microscope field was enumerated as usual using an inverted fluorescence microscope. Values given in the table represent means ± SD of 6 experiments with each experiment being the mean value of 3 replicate wells.
*Significantly (p<0.05) greater than control adherence. Control (absence of sugar) = 39 ± 8 pneumococci.

Discussion

Pneumococcal pneumonia is characterized by the appearance of bacteria closely lining the alveolar epithelium. Based on the ability of pneumococci to adhere to mixed lung cells (predominately type I alveolar cells) and purified type II cells, it appears that *S. pneumoniae adheres preferentially to the type II lung cell (LC)*. This suggested that the A549 type II LC line could serve as a valid model for pneumococcal attachment in the diseased lung. Using an in vitro adherence assay to a type II LC line several aspects of the mechanism of this interaction have been elucidated. Pneumococcal binding to cultures of LC was dose-dependent, rapid, did not require the bacteria to be metabolically active and was unaffected by the presence of several types of capsule. These findings are entirely in accord with previous studies of pneumococcal attachment to human vein endothelial cells (Geelen et al., 1993, Infect. Immun. 61:1538), suggesting similarities in the process of adherence to the two cells types. The interaction between pneumococci and endothelial cells has been shown to involve two separate mechanisms: ~60% of the bacterial adherence is mediated by cell-wall dependent mechanisms with the remaining 40% being protein mediated (Geelen et al., 1993, Infect. Immun. 61:1538). This study demonstrates that, like EC, approximately half of the pneumococcal attachment to LC involves a cell wall-dependent mechanism. In neither case is the phosphorylcholine determinant on the pneumococcal teichoic acid critical to adherence.

Like many classical mucosal pathogens, pneumococci can recognize and attach to glycoconjugates (Andersson et al., 1983, J. Exp. Med. 158:559; Krivan et al., 1988, Proc. Natl. Acad. Sci. USA 85:6157). The finding that inhibition of LC and EC cell surface glycosylation by tunicamycin significantly decreased pneumococcal adherence indicates the potential relevance of carbohydrate binding in the context of eukaryotic cells. This Example discloses the carbohydrate specificity of the glycoconjugate receptors on cultured LC and EC that interact with pneumococci. Several lines of evidence indicate that both LC and EC possess two separate classes of glycoconjugate-containing receptors whose minimal units consist of mannose linked to the disaccharides GalNAcβ1-4Gal or GalNAcβ1-3Gal. Carbohydrates that mimicked the receptors (as indicated by the ability to block adherence when preincubated with pneumococcus) included mannose, N-acetyl-D-galactosamine (GalNAc), galactose (Gal; EC only), asialo-GM1, asialo-GM2, forssman glycolipid and globoside. Pneumococci were also able to bind directly to these carbohydrates when immobilized on microtitre plates, but much less so or not at all and glycoconjugates tested.

Most importantly, the incubation of cultured LC and EC bearing adherent bacteria with GalNAc, mannose, asialo-GM2 or globoside caused elution of the adherent pneumococci. A combination of asialo-GM2 and globoside produced significantly greater antiadherence effects for both LC and EC than when either glycoconjugate was used alone. This suggested that these glycoconjugates defined independent receptors. In addition, the antiadherence effects of purified pneumococcal cell wall were not additive with asialo-GM2 but were additive with globoside in both cell types. Pneumococcal adherence to EC and LC involves bacterial cell wall-dependent and independent (protein) mechanisms. The results of this study suggest that the asialo-GM2 specificity recognizes the cell wall component and globoside, the protein component.

Figure 5A:
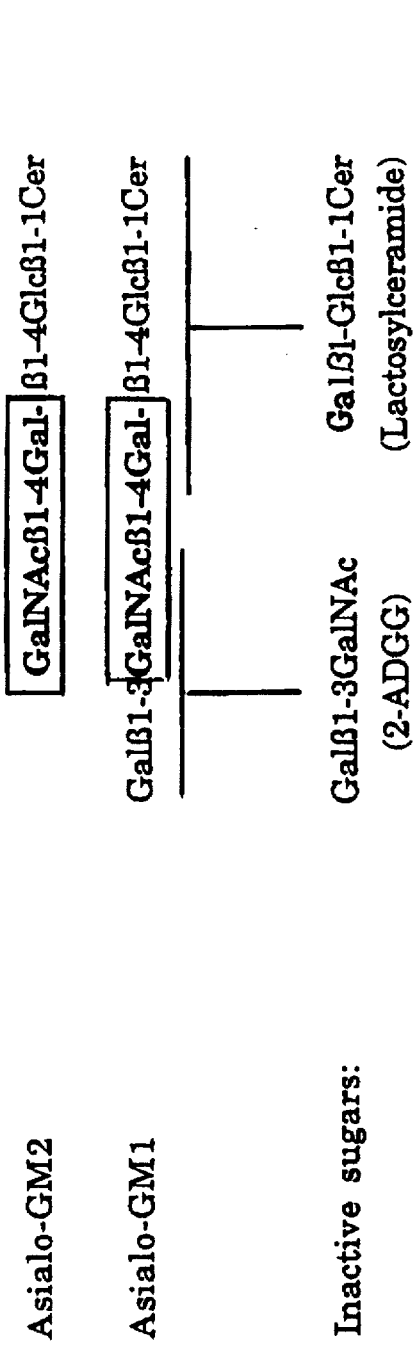
Figure 5B:
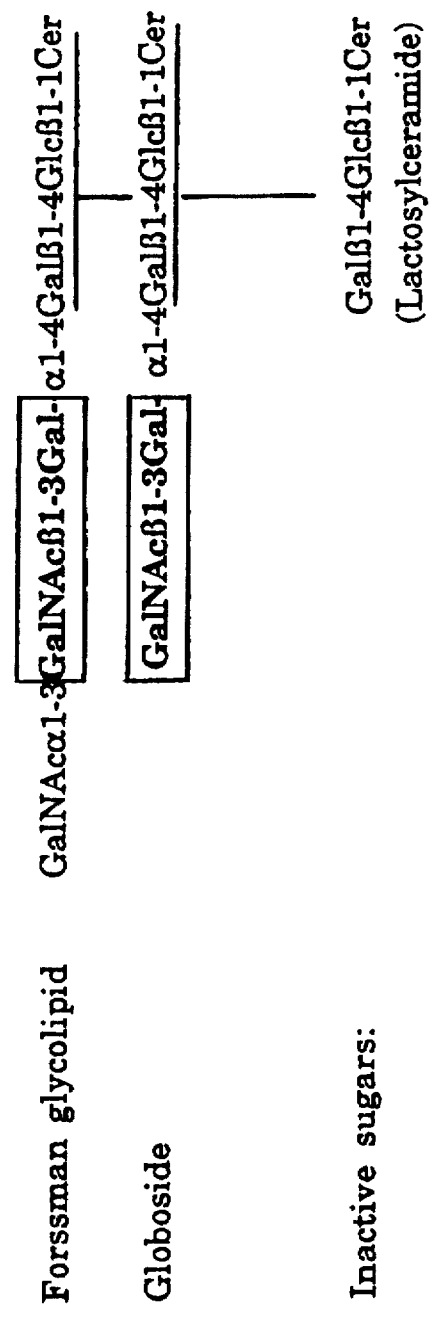

The two pneumococcal receptor specificities consisted of the same saccharide substituents linked in distinctly different stereochemical configurations: GalNAc linked in either a β1-4 or a β1-3 linkage to Gal (FIG. 5). A combination of two β1-4 GalNAc-Gal linked sugars, asialo-GM1 and asialo-GM2 possessed no greater antiadherence activity than either used singly. This was also true of the two β1-3 GalNAc-Gal linked sugars, forssman glycolipid and globoside. However, combinations across the two classes eliminated adherence. These two pairs of glycoconjugates therefore appear to define two separate classes of receptor (FIG. 5, A and B). The minimal receptor unit for each backbone was further defined by testing core structures and substituted variants for antiadherence effects. The core lactosylceramide (Galβ1-4Glc-1-1-Cer) and the inverted disaccharide 2-ADGG (Galβ1-3GalNAc) were inactive in both cell types, and Gal was only minimally active in EC. No permissive substitutions to asialo-GM2 were found (addition of a terminal Gal or internal sialic acid decreased activity), thus defining the minimal active unit for this receptor as GalNAcβ1-4Gal (FIG. 5A). Similar analysis suggested the GalNAcβ1-3Gal structure as the second minimal receptor unit with a more permissive substitution pattern for the LC as compared to the EC (FIG. 5B). Addition of a terminal GalNAcα1,4-linked to GalNAcβ1-3Gal increased the receptor activity for LC but decreased its efficacy in EC. This indicates that subtle differences exist between the receptor structures on these two cell types.

The ability of bacteria to recognize both internal and terminal carbohydrate sequences has been previously described (Krivan et al., 1988, Proc. Natl. Acad. Sci. USA 85:6157; Karlssen, 1989, Annu. Rev. Biochem. 58:309). Mannose is frequently present in the core of N-linked saccharides of glycoproteins, a finding which could explain the predicted presence of mannose in each receptor identified in this study. Mannose was not additive when used in combination with either GalNAc, GalNAcβ1-4Gal- or GalNAcβ1-3Gal-containing sugars, suggesting that it is present in both pneumococcal receptors on LC and EC. A large number of mannose-binding bacteria have been described (Gbarah et al., 1993, Infect. Immun. 61:1687). Since mannose has not been detected in the glycolipids of higher animals, it has been suggested that the bacteria which bind mannose may selectively recognize glycoproteins (Karlssen, 1989, Annu. Rev. Biochem. 58:309).

In agreement with Krivan and colleagues (Krivan et al., 1988, Proc. Natl. Acad. Sci. USA 85:6157), this study demonstrates that pneumococci can specifically attach to immobilized glycoconjugates containing the sequence GalNAcβ1-4Gal, including asialo-GM1 and asialo-GM2 and that sialylation of this sequence reduces binding. This study further indicates that this structure functions as a minimal receptor sequence on LC and EC for a pneumococcal cell wall determinant. Of these glycolipids, asialo-GM1 has been shown to be present on human lung epithelial cells (Krivan et al., supra). Sialylated glycoproteins containing GalNAcβ1-4Gal sequences are also present in a number of secretions and are able to bind bacteria when the sialic acid is cleaved off (Krivan et al., supra). It has been suggested that neuraminidase activity associated with influenza virus may increase the adherence of pneumococcus to the respiratory tract in vivo (Plotowski, 1986, Am. Rev. Respir. Dis. 134:1040). Studies by Andersson and colleagues (Andersson et al., 1983, J. Exp. Med. 158:559) using human nasopharyngeal cells identified a pneumococcal receptor possessing a minimum sequence of GlcNAcβ1-3Gal.

This structure is present in the saccharide chains of many glycolipids and glycoproteins including blood group antigens (Hakamori, 1981, Semin. Hematol. 18:39). In our studies the monosaccharide GlcNAc possessed no antiadherence activity for EC and LC, although pneumococci were able to bind directly to GlcNAc immobilized on microliter plates. Thus, this receptor specificity may play a role in the nasopharynx that is distinct from that in the lung.

This study identified a new receptor specificity for pneumococcal adherence: #GalNAcβ1-3Gal, which was involved in ~50% of the adherence to both LC and EC and appeared to interact with structures independent of the cell wall on the pneumococcal surface. Krivan and colleagues (Krivan et al., 1988, Proc. Natl. Acad. Sci. USA 85:6157) failed to detect binding of pneumococci to surfaces coated with the β1-3 sugars, including forssman glycolipid or globoside.

This discrepancy could result from the requirement for a 10-fold greater concentration of globoside than asialo-GM2 to detect binding. Since both GalNAcβ1-3Gal and GalNAcβ1-4Gal containing glycoconjugates were required to elute pneumococci from LC and EC, both receptors appear to be physiologically relevant. This underlines the importance of using living cells to determine the relative contributions of host glycoconjugate receptors to bacterial adherence.

Furthermore, therapeutic application of saccharides to promote clearance of pneumococci from the lower respiratory tract preferably interrupts interactions with both β1-4 and β1-3 GalNAc-Gal receptors.

EXAMPLE: SPECIFICITY OF ADHERENCE TO ACTIVATED CELLS

As discussed above, during the course of pneumococcal infection, pneumococci interact sequentially with nasopharyngeal cells, followed by lung epithelial cells (leading to pneumonia) or endothelial cells (leading to bacteremia, sepsis, and meningitis). Resting epithelial and endothelial cells bear two classes of glycoproteins bearing saccharide groups specific for binding pneumococci: GalNAcβ1-3Gal and GalNAcβ1-4Gal.

Figure 6A:
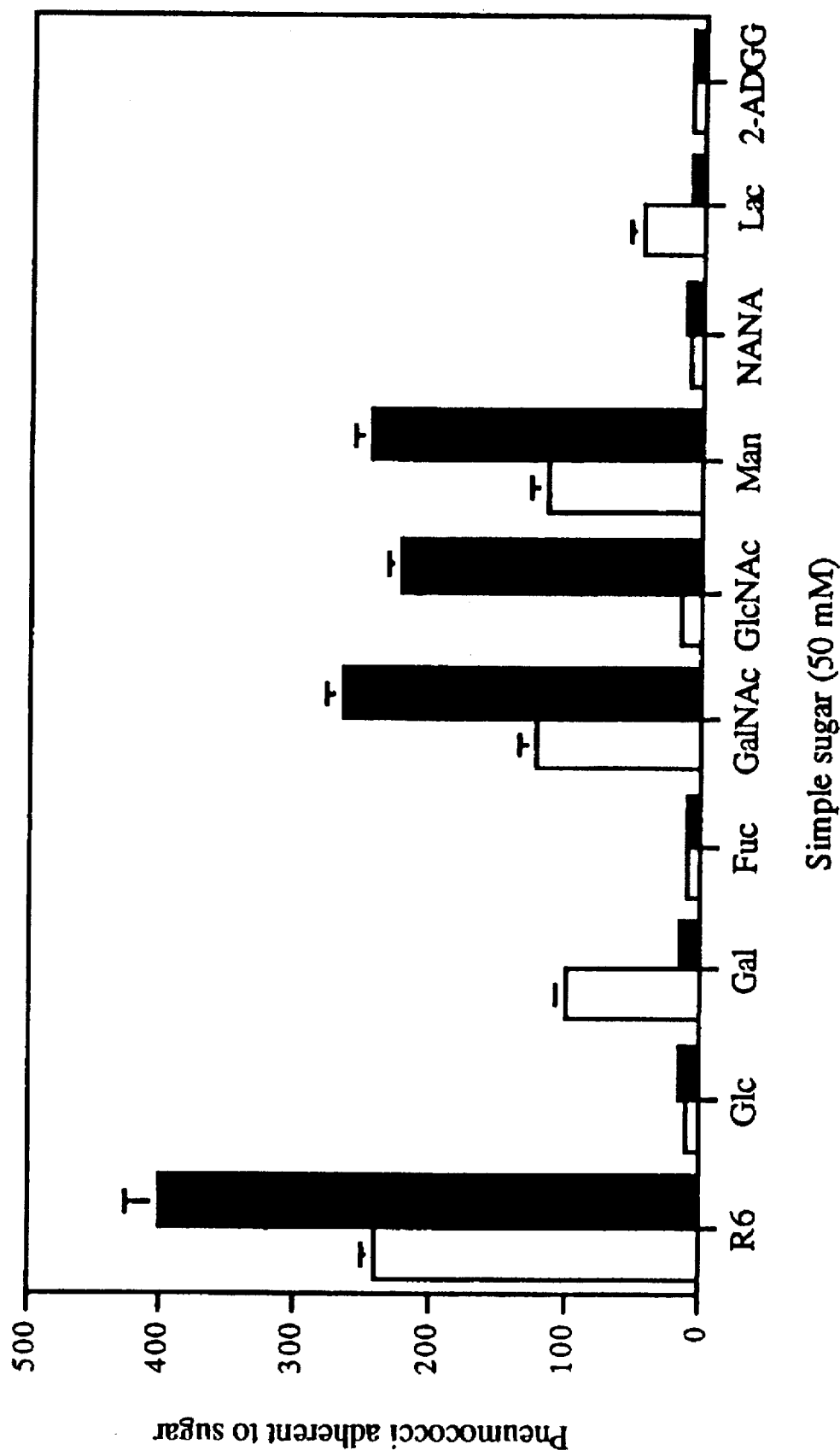
Figure 6B:
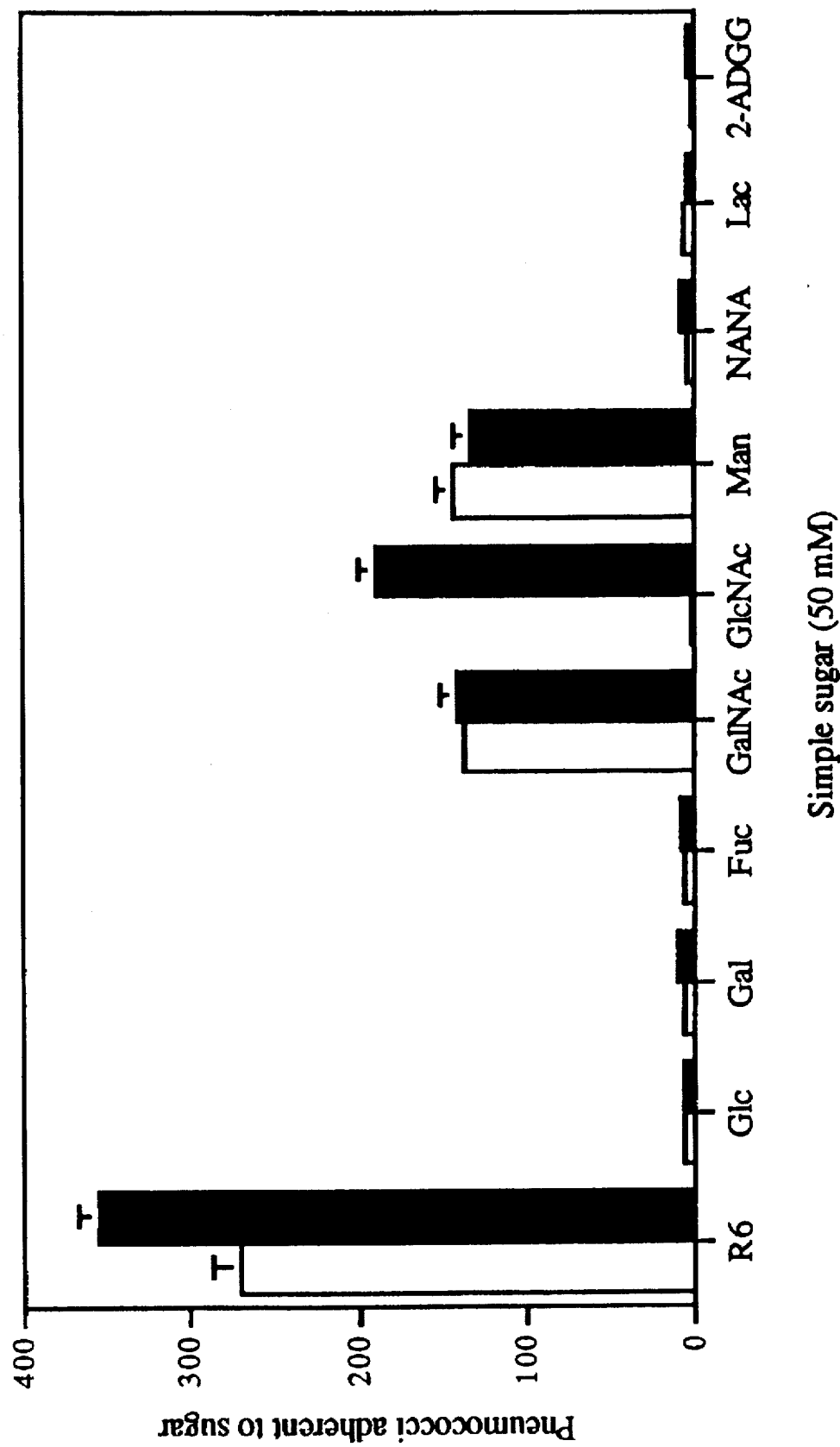
Figure 7:
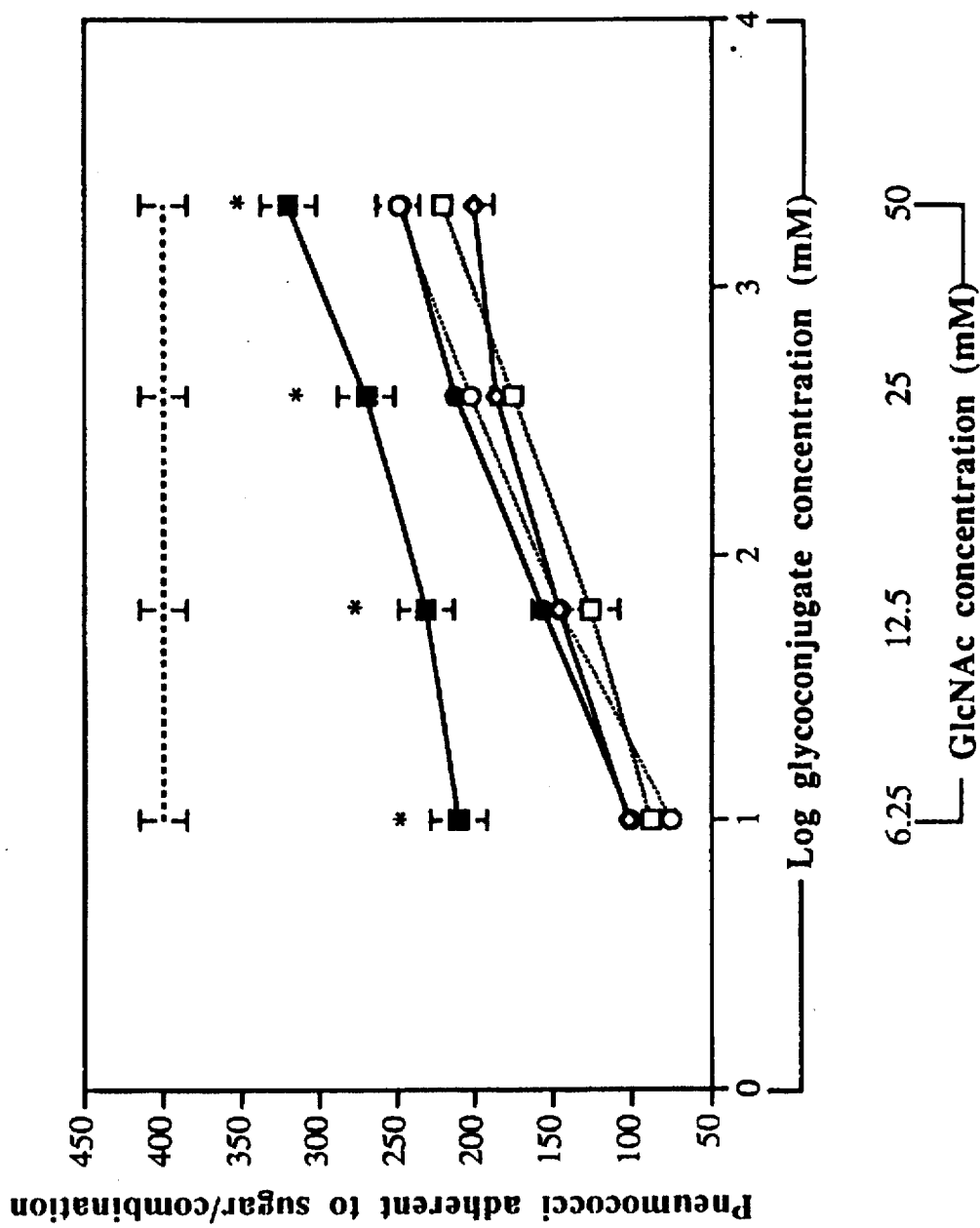

Pneumococcal infection is associated with the release of inflammatory cytokines, including tumor necrosis factor (TNF) and interleukin-1 (IL-1). Cytokine activation of human vein endothelial cells and type II lung cells resulted in greatly enhanced pneumococcal adherence. In a TNF or IL-1 activated cell, a new saccharide specificity appears: N-acetyl-D-glucosamine (GlcNAc) (see FIG. 6). GlcNAc-binding activity is associated with the GalNAcβ1-3Gal glycoprotein cell population (see FIG. 7).

The contribution of carbohydrate recognition to pneumococcal adherence to cytokine-stimulated EC and LC was tested using competition assays performed in the presence of monosaccharides (1–50 mM) or glycoconjugates (0.003–2 mM). Bacteria were pre-incubated for 15 min at room temperature with final concentrations of the sugars as stated, centrifuged (3,000 rpm, 3 min) to remove unbound sugar, resuspended to $1 \times 10^7$ cfu/ml in albumin buffer and added to the adherence assay. Comparison of the ability of single sugars (Tuomanen et al., J. Exp. Med. 168:267), to inhibit adherence indicated that while GalNAc and D-mannose were effective in resting cells, GlcNAc became effective in activated cells (FIG. 4).

Resting EC and LC express two classes of pneumococcal receptors containing GalNAcβ1-4Gal or GalNAcβ1-3Gal on a mannose core. These two receptor specificities are best defined by the inhibitory activities of the glycoconjugate asialo-GM2 for the β1-4 receptor and globoside for the β1-3 receptor. Cytokine stimulation of EC and LC resulted in a greater number of both of these resting cell receptors, and the appearance of the new GlcNAc specificity. This latter specificity was independent of the GalNAcβ1-4Gal specificity since the inhibitors were additive; GlcNAc was related to the GalNAcβ1-3Gal receptor population as these inhibitors were not additive (FIG. 5). If the effects of the sugars were non-additive then they were considered to occupy the same or linked receptors; if additive then they were interpreted to be present in separate receptors.

This invention may be embodied in other forms or carried out in other ways without departing from the spirit or essential characteristics thereof. The present disclosure is therefore to be considered as in all respects illustrative and not restrictive, the scope of the invention being indicated by the appended claims, and all changes which come within the meaning and range of equivalency are intended to be embraced therein.

Various references are cited throughout this specification, each of which is incorporated herein by reference in its entirety.

What is claimed is:

1. A pharmaceutical composition comprising an amount of a carbohydrate containing a disaccharide N-acetyl-D-galactosamine β1-3Gal motif effective to induce elution of adherent Streptococcus pneumoniae from host cells, an amount of a second carbohydrate containing a disaccharide N-acetyl-D-galactosamine β1-4Gal motif effective to induce elution of adherent S. pneumoniae from host cells, and a pharmaceutically acceptable carrier.

2. The pharmaceutical composition of claim 1, further comprising an amount of a second carbohydrate containing an N-acetyl-D-glucosamine motif effective to induce elution of adherent S. pneumoniae from host cells.

3. The pharmaceutical composition of claim 1 or 2 in which the carbohydrate is selected from the group consisting of forssman glycolipid and globoside.

4. The pharmaceutical composition of claim 1 in which the third carbohydrate is N-acetyl-D-glucosamine.

5. The pharmaceutical composition of claim 1 or 2 further comprising an amount of a carbohydrate selected from the group consisting of mannose, N-acetyl-galactose, mannose-D-mannose, and methyl-α-D-mannopyranoside effective to inhibit binding of S. pneumoniae to host cells.

6. The pharmaceutical composition according to claim 1 or 2 in which the carbohydrate or carbohydrates are multivalent.

7. The pharmaceutical composition of claim 1 or 2, in which the pharmaceutical composition is an aerosol formulation, which formulation contains a dispersant.

8. The pharmaceutical composition of claim 7 in which the dispersant is a surfactant.

9. The pharmaceutical composition of claim 7, which is a dry powder aerosol formulation, in which the carbohydrate or carbohydrates are present in finely divided powder.

10. The pharmaceutical composition of claim 9 which further comprises a bulking agent.

11. The pharmaceutical composition of claim 7, which is a liquid aerosol formulation further comprising a pharmaceutically acceptable diluent.

12. The pharmaceutical composition of claim 11 in which the diluent is selected from the group consisting of sterile water, saline, buffered saline, and dextrose solution.

13. The pharmaceutical composition of claim 1 or 2 in which the host cell is selected from the group consisting of lung epithelial cells and vascular endothelial cells.

14. A method for preventing or treating an infection with S. pneumoniae comprising administering to a subject in need of treatment for an infection with *S. pneumoniae* an amount of a carbohydrate containing a disaccharide N-acetyl-D-galactosamine β1-3Gal motif effective to induce elution of adherent *S. pneumoniae* from host cells.

15. The method according to claim 14, further comprising administering an amount of a second carbohydrate containing a disaccharide N-acetyl-D-galactosamine β1-4Gal motif effective to induce elution of adherent *S. pneumoniae* from host cells.

16. The method according to claim 14, further comprising administering an amount of a second carbohydrate containing an N-acetyl-D-glucosamine motif effective to induce elution of adherent *S. pneumoniae* from host cells.

17. The method according to claim 14, further comprising administering an amount of a third carbohydrate containing an N-acetyl-D-glucosamine motif effective to induce elution of adherent *S. pneumoniae* from host cells.

18. The method according to claim 14, 15, 16 or 17 in which the carbohydrate is selected from the group consisting of forssman glycolipid and globoside.

19. The method according to claim 15 or 17 in which the second carbohydrate is selected from the group consisting of asialo-GM1 and asialo-GM2.

20. The method according to claim 17 in which the third carbohydrate is N-acetyl-D-glucosamine.

21. The method according to claim 14, 15, 16, or 17 further comprising administering an amount of a carbohydrate selected from the group consisting of mannose, N-acetyl-galactose, mannose-D-mannose, and methyl-α-D-mannopyranoside effective to inhibit binding of *S. pneumoniae* to host cells.

22. The method according to claim 14, 15, 16 or 17 in which the carbohydrate or carbohydrates are multivalent.

23. The method according to claim 14, 15, 16, or 17 in which the administering comprises atomizing and inhaling the carbohydrate or carbohydrates.

24. The method according to claim 23 in which the atomizing is nebulizing.

25. The method according to claim 14, 15, 16, or 17 in which the administering comprises injecting the carbohydrate or carbohydrates intravenously.

26. A method for detecting the presence of *S. pneumoniae* in a sample from a subject comprising detecting the binding of a carbohydrate containing a disaccharide N-acetyl-D-galactosamine β1-3Gal motif to *S. pneumoniae*.

27. The method according to claim 26, further comprising detecting the binding of a second carbohydrate containing a disaccharide N-acetyl-D-galactosamine β1-4Gal motif to *S. pneumoniae*.

28. The method according to claim 26, further comprising detecting the binding of a third carbohydrate containing an N-acetyl-D-glucosamine *S. pneumoniae* bacteria.

29. The method according to claim 27, further comprising detecting the binding of a third carbohydrate containing an N-acetyl-D-glucosamine *S. pneumoniae* bacteria.

30. The method according to claim 26, 27, 28, or 29 in which the carbohydrate is selected from the group consisting of forssman glycolipid and globoside.

31. The method according to claim 27 or 29 in which the second carbohydrate is selected from the group consisting of asialo-GM1 and asialo-GM2.

32. The method according to claim 28 or 29 in which the third carbohydrate is N-acetyl-D-glucosamine.

33. The method according to claim 26, 27, 28, or 29 in which the carbohydrate or carbohydrates are multivalent.

34. The method according to claim 26, 27, 28, or 29 in which at least one carbohydrate is labeled.

35. The method according to claim 26, 27, 28, or 29 in which at least one carbohydrate is attached to a solid phase support.

36. A kit for detecting the presence of *S. pneumoniae* in a sample from a subject comprising:
(a) a carbohydrate containing a disaccharide N-acetyl-D-galactosamine β1-3Gal motif; and
(b) means for detecting binding of the *S. pneumoniae* bacterium in a sample from the subject.

37. The kit of claim 36, further comprising:
(c) a second carbohydrate containing a disaccharide N-acetyl-D-galactosamine β1-4Gal motif; and
(d) means for detecting binding of the second carbohydrate to the *S. pneumoniae*.

38. The kit of claim 36, further comprising:
(e) a second carbohydrate containing a disaccharide N-acetyl-D-glucosamine motif; and
(f) means for detecting binding of the third carbohydrate to the *S. pneumoniae*.

39. The kit of claim 37, further comprising:
(e) a third carbohydrate containing a disaccharide N-acetyl-D-glucosamine motif; and
(f) means for detecting binding of the third carbohydrate to the *S. pneumoniae*.

40. The kit of claim 36, 37, 38, or 39 in which at least one carbohydrate is labelled.

41. The kit of claim 36, 37, 38, or 39 in which at least one carbohydrate is attached to a solid phase support.

42. The method according to claim 16 in which the second carbohydrate is N-acetyl-D-glucosamine.

* * * * *